(12) United States Patent
Cahalane et al.

(10) Patent No.: US 10,010,315 B2
(45) Date of Patent: Jul. 3, 2018

(54) TISSUE ANCHORS AND PERCUTANEOUS TRICUSPID VALVE REPAIR USING A TISSUE ANCHOR

(71) Applicant: Mitralign, Inc., Tewksbury, MA (US)

(72) Inventors: Steven Cahalane, Pelham, NH (US); Jason Robinson, Windham, NH (US); Morgan House, Newfields, NH (US)

(73) Assignee: Mitralign, Inc., Tewksbury, MA (US)

( * ) Notice: Subject to any disclaimer, the term of this patent is extended or adjusted under 35 U.S.C. 154(b) by 357 days.

(21) Appl. No.: 14/662,203

(22) Filed: Mar. 18, 2015

(65) Prior Publication Data

US 2016/0270916 A1 Sep. 22, 2016

(51) Int. Cl.

| A61B 17/04 | (2006.01) |
|---|---|
| A61F 2/24 | (2006.01) |
| A61B 17/064 | (2006.01) |
| A61B 17/02 | (2006.01) |
| A61B 17/00 | (2006.01) |
| A61B 17/22 | (2006.01) |
| A61B 90/00 | (2016.01) |

(52) U.S. Cl.
CPC ...... *A61B 17/0401* (2013.01); *A61B 17/0218* (2013.01); *A61B 17/0644* (2013.01); *A61B 2017/003* (2013.01); *A61B 2017/00026* (2013.01); *A61B 2017/00783* (2013.01); *A61B 2017/00876* (2013.01); *A61B 2017/0237* (2013.01); *A61B 2017/0406* (2013.01); *A61B 2017/0409* (2013.01); *A61B 2017/0417* (2013.01); *A61B 2017/22038* (2013.01); *A61B 2090/3966* (2016.02); *A61F 2/2442* (2013.01); *A61F 2/2466* (2013.01); *A61F 2220/0008* (2013.01)

(58) Field of Classification Search
CPC .. A61B 2017/00783; A61B 2017/0404; A61B 2017/0409; A61B 2017/0417; A61B 2017/0419; A61B 17/0401
See application file for complete search history.

(56) References Cited

U.S. PATENT DOCUMENTS

| 5,332,402 A | 7/1994 | Teitelbaum |
| 5,364,408 A | 11/1994 | Gordon |

(Continued)

FOREIGN PATENT DOCUMENTS

| CN | 102869318 | 1/2013 |
| WO | WO 2008/112740 | 9/2008 |

(Continued)

*Primary Examiner* — Christopher L Templeton
(74) *Attorney, Agent, or Firm* — Leason Ellis LLP

(57) ABSTRACT

The present teachings provide devices and methods of treating a tricuspid valve regurgitation. Specifically, one aspect of the present teachings provides devices and methods of identifying a suitable location on the tricuspid annulus, placing a wire across the tricuspid annulus at such an identified location, deploying a tissue anchor across such an identified location, deploying two or more tissue anchors and coupling the tissue anchors with a flexible tensioning member, and applying tension to a flexible tensioning member that is coupled with the two or more tissue anchors, plicating tissues between each pair of the two or more tissue anchors, and reducing the circumference of the tricuspid annuls. As a result, a regurgitation jet is reduced or eliminated.

19 Claims, 35 Drawing Sheets

(56) References Cited

U.S. PATENT DOCUMENTS

| | | | |
|---|---|---|---|
| 5,733,331 A | 3/1998 | Peredo | |
| 5,810,746 A | 9/1998 | Goldstein et al. | |
| 6,048,351 A | 4/2000 | Gordon | |
| 6,074,417 A | 6/2000 | Peredo | |
| 6,629,534 B1 | 10/2003 | St. Goar | |
| 7,431,726 B2 | 10/2008 | Spence et al. | |
| 8,029,556 B2 | 10/2011 | Rowe | |
| 8,382,829 B1 * | 2/2013 | Call | A61B 17/0401 623/2.37 |
| 8,475,525 B2 | 7/2013 | Maisano et al. | |
| 8,845,717 B2 | 9/2014 | Khairkhahan et al. | |
| 8,888,843 B2 | 11/2014 | Khairkhahan et al. | |
| 8,961,594 B2 | 2/2015 | Maisano et al. | |
| 8,961,596 B2 | 2/2015 | Maisano et al. | |
| 2002/0107531 A1 | 8/2002 | Schreck et al. | |
| 2003/0120340 A1 | 6/2003 | Liska et al. | |
| 2003/0199974 A1 | 10/2003 | Lee | |
| 2004/0162610 A1 | 8/2004 | Liska et al. | |
| 2004/0225233 A1 * | 11/2004 | Frankowski | A61M 25/0127 600/585 |
| 2005/0119734 A1 | 6/2005 | Spence et al. | |
| 2005/0267571 A1 | 12/2005 | Spence | |
| 2006/0229708 A1 | 10/2006 | Powell et al. | |
| 2007/0010857 A1 | 1/2007 | Sugimoto et al. | |
| 2007/0112425 A1 | 5/2007 | Schaller | |
| 2008/0086164 A1 | 4/2008 | Rowe | |
| 2009/0076547 A1 | 3/2009 | Sugimoto | |
| 2009/0093670 A1 | 4/2009 | Annest et al. | |
| 2009/0292353 A1 | 11/2009 | Yoganathan et al. | |
| 2010/0063586 A1 | 3/2010 | Hasenkam | |
| 2010/0070028 A1 | 3/2010 | Sugimoto | |
| 2010/0210899 A1 | 8/2010 | Schankereli | |
| 2010/0292785 A1 | 11/2010 | Seguin et al. | |
| 2011/0015476 A1 | 1/2011 | Franco | |
| 2011/0060407 A1 | 3/2011 | Ketai | |
| 2011/0071626 A1 | 3/2011 | Wright | |
| 2011/0184510 A1 | 7/2011 | Maisano et al. | |
| 2012/0029627 A1 | 2/2012 | Salahieh et al. | |
| 2012/0035712 A1 | 2/2012 | Maisano et al. | |
| 2012/0203336 A1 | 8/2012 | Annest | |
| 2012/0310840 A1 | 12/2012 | Colombo et al. | |
| 2013/0018459 A1 | 1/2013 | Maisano et al. | |
| 2013/0046380 A1 | 2/2013 | Maisano et al. | |
| 2014/0114390 A1 | 4/2014 | Tobis et al. | |
| 2014/0243859 A1 | 8/2014 | Robinson | |
| 2014/0243894 A1 | 8/2014 | Groothuis et al. | |
| 2014/0350662 A1 | 11/2014 | Vaturi | |
| 2015/0025553 A1 | 1/2015 | Del Nido et al. | |
| 2015/0112429 A1 | 4/2015 | Khairkhahan et al. | |
| 2015/0119936 A1 | 4/2015 | Gilmore et al. | |
| 2015/0119979 A1 | 4/2015 | Maisano et al. | |
| 2015/0164637 A1 | 6/2015 | Khairkhahan et al. | |

FOREIGN PATENT DOCUMENTS

| | | |
|---|---|---|
| WO | WO 2012/004679 | 1/2012 |
| WO | WO 2012/178115 | 12/2012 |
| WO | WO 2014/134183 | 9/2014 |

* cited by examiner

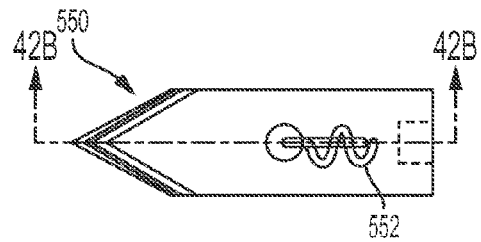
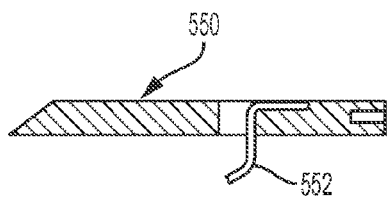
FIG. 20E  FIG. 20F
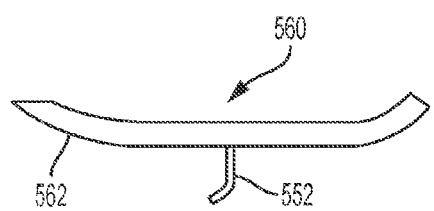
FIG. 20G
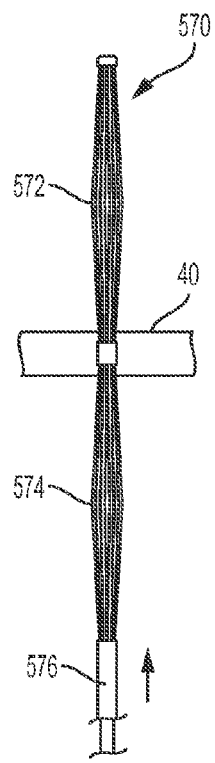
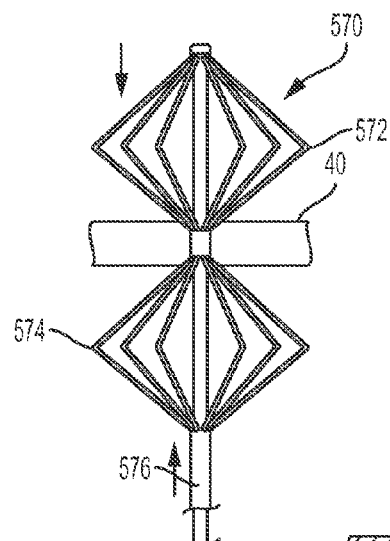
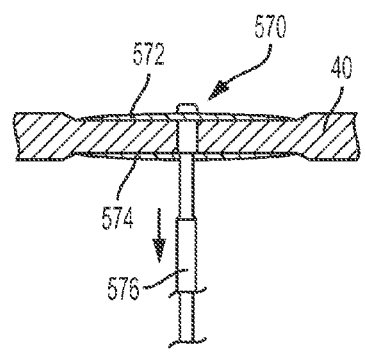
FIG. 20H  FIG. 20I  FIG. 20J

TISSUE ANCHORS AND PERCUTANEOUS TRICUSPID VALVE REPAIR USING A TISSUE ANCHOR

FIELD

The present teachings generally relate to new tissue anchors and uses thereof in percutaneous valve repair.

BACKGROUND

Tricuspid valve diseases relate to conditions in which the valve between the two right heart chambers (i.e., the right ventricle and the right atrium) doesn't function properly and these diseases often occur with other heart valve problems. Examples of tricuspid valve diseases include tricuspid valve regurgitation, tricuspid valve stenosis, tricuspid valve atresia, and the Ebstein's anomaly. In tricuspid valve regurgitation, the tricuspid valve doesn't close properly and blood flows back into the right atrium; in tricuspid valve stenosis, the tricuspid valve is narrowed and reduces the amount of blood flowing into the right ventricle; in tricuspid atresia, a congenital heart disease, a solid wall of tissues blocks the blood from flowing between the two right heart chambers; and in the Ebstein's anomaly, a malformed tricuspid valve situates at a position lower than the normal in the right ventricle and causes blood to flow back into the right atrium. There are other tricuspid valve diseases generally known to a person with ordinary skill in the art and these tricuspid valve diseases are also included in the present teachings.

A tricuspid valve disease can be corrected by an annuloplasty ring. In some instances, this device is preferred for surgically repairing a defect tricuspid valve. An annuloplasty ring is an anatomically-correct three-dimensional (3D) ring and can flexibly conform to the heart valve opening. This ring is implanted into a defect tricuspid valve and reduces the valve opening. Properly implanted, an annuloplasty ring allows the valve to open and close properly.

Tricuspid valve repair surgery can be done in one of two ways: a minimally invasive surgery or an open-heart surgery. A minimally invasive method involves making a small incision in the upper or lower chest and inserting a valve repairing system/device percutaneously. After the valve is repaired, the incision is closed with dissolving sutures. Comparing to an open-heart surgery, advantages of a minimally invasive approach include a shorter recovery time, less post-operation pain, and earlier return to work and normal daily activities.

However, there are drawbacks in valve replacement therapy and, as a result, needs exist for repairing a diseased tricuspid valve percutaneously.

SUMMARY

One aspect of the present teachings provides a method for percutaneously reducing the circumference of a tricuspid annulus. This method includes a number of steps, the sequence of which can be changed and each of which can be omitted or modified without the method falling outside the scope of the present teachings. An exemplary step includes positioning a wire delivery catheter through the tricuspid valve into the right ventricle. Another exemplary step includes contacting a distal end of the wire delivery catheter with the tricuspid annulus inside the right ventricle at a first location. Another exemplary step includes advancing one end of a wire from the right ventricle across the tricuspid annulus to the right atrium at the first location, where the wire tracks through an axial lumen of the wire delivery catheter. Another exemplary step includes capturing the end of the wire with a capture device deployed inside the right atrium. Another exemplary step includes retracting the capture device proximally to bring the end of the wire outside of the body. Another exemplary step includes tracking a first tissue anchor delivery catheter over the wire and extending the first tissue anchor delivery catheter across the tricuspid annulus so that a distal end of the first tissue anchor delivery catheter resides inside the right ventricle. Another exemplary step includes deploying a first tissue anchor with a portion of the tissue anchor positioning against the tricuspid annulus from inside the right ventricle. Another exemplary step includes deploying a first tissue anchor with a portion of the tissue anchor positioning against the tricuspid annulus from inside the right atrium. Another exemplary step includes deploying a first tissue anchor with a distal portion of the tissue anchor positioning against the tricuspid annulus from inside the right ventricle and a proximal portion of the tissue anchor positioning against the tricuspid annulus from inside the right atrium. Another exemplary step includes retracting the end of the wire back into the axial lumen of the wire delivery catheter.

Another exemplary step includes positioning the wire delivery catheter with the distal end of the wire delivery catheter contacting the tricuspid annulus inside the right ventricle at a second location. Another exemplary step includes advancing the end of the wire from the right ventricle across the tricuspid annulus to the right atrium. Another exemplary step includes capturing the end of the wire with a capture device deployed inside the right atrium. Another exemplary step includes retracting the capture device proximally and thereby extending the end of the wire outside of the body. Another exemplary step includes tracking a second tissue anchor delivery catheter over the wire. Another exemplary step includes extending the second tissue anchor delivery catheter across the tricuspid annulus at the second location so that a distal end of the second tissue anchor delivery catheter resides inside the right ventricle. Another exemplary step includes deploying a second tissue anchor with a portion of the tissue anchor positioning against the tricuspid annulus from inside the right ventricle. Another exemplary step includes deploying a second tissue anchor with a portion of the tissue anchor positioning against the tricuspid annulus from inside the right atrium. Another exemplary step includes deploying a second tissue anchor with a distal portion of the tissue anchor positioning against the tricuspid annulus from inside the right ventricle and a proximal portion of the tissue anchor positioning against the tricuspid annulus from inside the right atrium. Another exemplary step includes reducing the distance between the first and second tissue anchors.

In other embodiments, a method for percutaneously reducing the circumference of a tricuspid annulus includes a number of other steps, the sequence of which can be changed and each of which can be omitted or modified without the method falling outside the scope of the present teachings. An exemplary step includes positioning a locating catheter through the tricuspid valve into the right ventricle. Another exemplary step includes contacting a distal end of the locating catheter with the tricuspid annulus inside the right ventricle at a first location. Another exemplary step includes advancing a wire delivery catheter into the right atrium with a distal end of the wire delivery catheter opposing the distal end of the locating catheter and contacting the tricuspid annulus inside the right atrium at the first location. Another exemplary step includes advancing a distal end of a wire from the right atrium across the tricuspid annulus to the right ventricle at the first location, wherein the wire tracks through an axial lumen of the wire delivery catheter. Another exemplary step includes tracking a first tissue anchor delivery catheter over the wire. Another exemplary step includes crossing the tricuspid annulus with a distal end of the first tissue anchor delivery catheter inside the right ventricle. Another exemplary step includes deploying a first tissue anchor with a portion of the tissue anchor positioning against the tricuspid annulus from inside the right ventricle. Another exemplary step includes deploying a first tissue anchor with a portion of the tissue anchor positioning against the tricuspid annulus from inside the right atrium. Another exemplary step includes deploying a first tissue anchor with a distal portion of the tissue anchor positioning against the tricuspid annulus from inside the right ventricle and a proximal portion of the tissue anchor positioning against the tricuspid annulus from inside the right atrium. Another exemplary step includes retracting the distal end of the wire back into the axial lumen of the wire delivery catheter.

Another exemplary step includes positioning the locating catheter with the distal end of the locating catheter contacting the tricuspid annulus inside the right ventricle at a second location. Another exemplary step includes positing the wire delivery catheter into the right atrium with the distal end of the wire delivery catheter opposite to the distal end of the locating catheter and contacting the tricuspid annulus inside the right atrium at the second location. Another exemplary step includes advancing the distal end of the wire from the right atrium across the tricuspid annulus to the right ventricle. Another exemplary step includes tracking a second tissue anchor delivery catheter over the wire and crossing the tricuspid annulus at the second location with a distal end of the second tissue anchor delivery catheter inside the right ventricle. Another exemplary step includes deploying a second tissue anchor with a portion of the tissue anchor positioning against the tricuspid annulus from inside the right ventricle. Another exemplary step includes deploying a second tissue anchor with a portion of the tissue anchor positioning against the tricuspid annulus from inside the right atrium. Another exemplary step includes deploying a second tissue anchor with a distal portion of the tissue anchor positioning against the tricuspid annulus from inside the right ventricle and a proximal portion of the tissue anchor positioned against the tricuspid annulus from inside the right atrium. Another exemplary step includes reducing the distance between the first and second tissue anchors.

In other embodiments, a method for percutaneously reducing the circumference of a tricuspid annulus includes a number of steps, the sequence of which can be changed and each of which can be omitted or modified without the method falling outside the scope of the present teachings. An exemplary step includes positioning a wire delivery catheter through the tricuspid valve into the right ventricle, wherein a bident catheter is slidably disposed within a lumen of the wire delivery catheter, a first wire is slidably disposed within a first catheter member of the bident catheter, a second wire is slidably disposed within a second catheter member of the bident catheter. Another exemplary step includes positioning a distal end of the first catheter member at a first location. Another exemplary step includes advancing one end of the first wire from the right ventricle across the tricuspid annulus to the right atrium at the first location. Another exemplary step includes expanding the second catheter member of the bident catheter. Another exemplary step includes positioning a distal end of the second catheter member against the tricuspid annulus at a second location. Another exemplary step includes advancing one end of the second wire from the right ventricle across the tricuspid annulus to the right atrium at the second location. Another exemplary step includes capturing the ends of the first and second wires with a capture device. Another exemplary step includes retracting the capture device proximally and extending the ends of the first and second wires outside of the body. Another exemplary step includes tracking a first tissue anchor delivery catheter over the first wire and a second tissue anchor delivery catheter over the second wire. Another exemplary step includes the first and second tissue anchor delivery catheters crossing the tricuspid annulus with distal ends of the first and second tissue anchor delivery catheters inside the right ventricle. Another exemplary step includes deploying the first and second tissue anchors with portions of the first and second tissue anchors positioning against the tricuspid annulus from inside the right ventricle. Another exemplary step includes deploying the first and second tissue anchors with portions of the first and second tissue anchors positioning against the tricuspid annulus from inside the right atrium. Another exemplary step includes deploying the first and second tissue anchors with distal portions of the first and second tissue anchors positioning against the tricuspid annulus from inside the right ventricle and proximal portions of the first and second tissue anchors positioning against the tricuspid annulus from inside the right atrium. Another exemplary step includes reducing the distance between the first and second tissue anchors.

In other embodiments, a method for percutaneously reducing the circumference of a tricuspid annulus includes a number of steps, the sequence of which can be changed and each of which can be omitted or modified without the method falling outside of the present teachings. An exemplary step includes positioning a locating catheter through the tricuspid valve into the right ventricle, wherein a bident catheter is slidably disposed within a lumen of the locating catheter and the bident catheter has a first catheter member and a second catheter member. Another exemplary step includes positioning a distal end of the first catheter member at a first location. Another exemplary step includes expanding the second catheter member of the bident catheter and positioning a distal end of the second catheter member against the tricuspid annulus at a second location. Another exemplary step includes advancing a first and second wire delivery catheters into the right atrium with distal ends of the first and second wire delivery catheters positioned opposite to the distal ends of the first and second catheter member. Another exemplary step includes the first and second wire delivery catheters contacting the tricuspid annulus inside the right atrium at the first and second locations. Another exemplary step includes advancing distal ends of a first and second wires from the right atrium across the tricuspid annulus to the right ventricle at the first and second locations. Another exemplary step includes tracking the first and second tissue anchor delivery catheters over the first and second wires and crossing the tricuspid annulus with distal ends of the first and second tissue anchor delivery catheters inside the right ventricle. Another exemplary step includes deploying the first and second tissue anchors with portions of the first and second tissue anchors positioned against the tricuspid annulus from inside the right ventricle. Another exemplary step includes deploying the first and second tissue anchors with portions of the first and second tissue anchors positioned against the tricuspid annulus from inside the right atrium. Another exemplary step includes deploying the first and second tissue anchors with distal portions of the first and second tissue anchors positioned against the tricuspid annulus from inside the right ventricle and proximal portions of the first and second tissue anchors positioned against the tricuspid annulus from inside the right atrium. Another exemplary step includes reducing the distance between the first and second tissue anchors.

Another aspect of the present teachings relates to reducing the circumference of tricuspid valve by deploying two or more tissue anchors and/or fasteners and connecting these tissue anchors and/or fasteners with one or more tensioning member. In various embodiments, at least two of the two or more tissue anchors and/or fasteners are connected with a continuous portion of the tensioning member. In some embodiments, three of the two or more tissue anchors and/or fasteners are connected with a continuous portion of the tensioning member. In certain embodiments, all of the two or more tissue anchors and/or fasteners are connected with a continuous portion of the flexible tensioning member. In various embodiments, at least one of the two or more tissue anchors is configured to slide along the flexible tensioning member. This configuration can sometimes be referred to as a chained tissue anchor, i.e., each of the tissue anchors and fasteners being connected by a tensioning member, which is referred to as the chain or string.

In various embodiments, tension is applied to the tensioning member connecting to two or more tissue anchors and/fasteners of the present teachings, thereby reducing the distance between at least two of the tissue anchors and/fasteners. As a result, in some embodiments, the tissue between the at least two of the tissue anchors and/or fasteners is plicated. In certain embodiments, two or more distances, each of which is between two tissue anchors and/or fasteners of the present teachings, are reduced and the tissue between each pair of the tissue anchors and/or fasteners is plicated. This plication can sometimes be referred to as a chain plication. In various embodiments, the plication of tissue between the tissue anchors and/or fasteners reduces the circumference of tricuspid valve and eliminates or reduces the extent of tricuspid valve regurgitation.

Yet another aspect of the present teachings relates to various tissue anchors and/or fasteners. In various embodiments, a tissue anchor of the present teachings comprises a flexible anchor element coupled with a flexible tensioning member. For example, the flexible anchor can be made from a surgical grade fabric material and the flexible tensioning member can be a suture. In some embodiments, a first portion of the flexible anchor element is deployed at one side of the tricuspid valve, for example, the tricuspid annulus. In some embodiments, a second portion of the flexible anchor element is deployed at the other side of the tricuspid valve. In some embodiments, a third portion, for example, one adjacent to the first or second portion, of the flexible anchor element is deployed in or through an aperture in tricuspid tissue, for example, the tricuspid annulus. In various embodiments, a tissue anchor of the present teachings comprises a T-bar coupled with a tensioning member (sometimes referred to as a tail). In various embodiments, a tissue anchor of the present teachings comprises an anchor button coupled with a flexible tensioning member. In various embodiments, a tissue anchor of the present teachings comprises a fastener coupled with a flexible tensioning member. In various embodiments, a tissue anchor of the present teachings comprises two radially expandable portions. In various embodiments, a tissue anchor of the present teachings comprises a bar, a ribbon, and a flexible tensioning member where the ribbon is coupled with the bar, the flexible tensioning member, or both. Various other embodiments of tissue anchors can also be used to plicate a tricuspid annulus, effectively reducing the circumference of the tricuspid annulus and reducing or eliminating tricuspid regurgitation.

Yet another aspect of the present teachings relates to devices that can be used to deliver a tissue anchor of the present teaching and repair a tricuspid valve. A particular embodiment of the present teachings relates to a push wire having an elongate wire coupled with a holder, a rounded distal end, one or more than one marker, or a combination thereof.

DETAILED DESCRIPTION

Figure 1A:
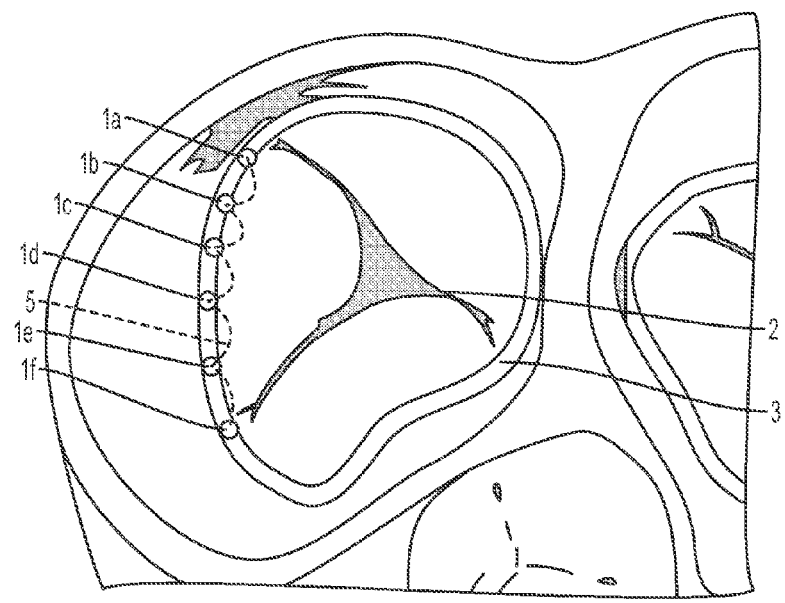
FIGS. 1A-1B are perspective views of an embodiment of the present teachings where tension is applied to multiple exemplary tissue anchors deployed across the tricuspid annulus in accordance with the present teachings.

Certain specific details are set forth in the following description and figures to provide an understanding of various embodiments of the present teachings. Those of ordinary skill in the relevant art would understand that they can practice other embodiments of the present teachings without one or more of the details described herein. Thus, it is not the intention of the Applicant(s) to restrict or in any way limit the scope of the appended claims to such details. While various processes are described with reference to steps and sequences in the following disclosure, the steps and sequences of steps should not be taken as required to practice all embodiments of the present teachings.

As used herein, the term "lumen" means a canal, a duct, or a generally tubular space or cavity in the body of a subject, including a vein, an artery, a blood vessel, a capillary, an intestine, and the like. The term "lumen" can also refer to a tubular space in a catheter, a sheath, a hollow needle, a tube, or the like.

As used herein, the term "proximal" shall mean close to the operator (less into the body) and "distal" shall mean away from the operator (further into the body). In positioning a medical device inside a patient, "distal" refers to the direction away from a catheter insertion location and "proximal" refers to the direction close to the insertion location.

As used herein, the term "wire" can be a strand, a cord, a fiber, a yarn, a filament, a cable, a thread, or the like, and these terms may be used interchangeably.

As used herein, the term "sheath" may also be described as a "catheter" and, thus, these terms can be used interchangeably.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and attached claims are approximations. At the very least and not as an attempt to limit the application of the doctrine of equivalents to the scope of the attached claims, numerical parameters should be read in light of the number of reported significant digits and the application of ordinary rounding techniques.

The present teachings relate to devices and methods for treating a tricuspid valve regurgitation percutaneously. Although referring to FIGS. 1 to 29, a person with ordinary skill in the art would recognize that the figures and description thereto refer to various embodiments of the present teachings and, unless indicated otherwise by their contexts, do not limit the scope of the attached claims to the figures and/or description thereto.

Headings and subheadings are used herein solely for the convenience of disclosure and discussion, and, thus, do not in any way limit the scope of the attached claims.

Reducing Circumference of Tricuspid Valve

An aspect of the present teachings relates to methods of reducing the circumference of a tricuspid valve (2). For example, now referring to FIGS. 1A and 1B in general, the circumference of a tricuspid valve (2) can be reduced by deploying a plurality of connected tissue anchors or fasteners (1a, 1b, 1c, 1d, 1e, 1f) of the present teachings around the tricuspid annulus (3), and applying tension to the tensioning member to plicate tissues between each pair of tissue anchors/fasteners.

Specifically, as illustrated in FIG. 1A, according to some embodiments, the first tissue anchor (1a) is deployed at a location in or near the tricuspid annulus (3). This is repeated as many times as necessary to deploy a necessary number of tissue anchors. Referring again to FIG. 1A, the first tissue anchor (1a) is deployed at a location at or close to the commissure of the posterior and septal leaflets and the second to fifth tissue anchors (1b, 1c, 1d, 1e) are deployed at locations distributed between the commissure of the posterior and septal leaflets and the commissure of the posterior and anterior leaflets, as illustrated in FIG. 1A. In some embodiments, a sixth tissue anchor (1f) is deployed in the anterior annulus at or close to the commissure of the posterior and anterior leaflets, as illustrated in FIG. 1A.

In various embodiments, two or more of the tissue anchors (1a-1f) are connected with a tensioning member (5).

In some embodiments, two of the tissue anchors are connected with a tensioning member (5). In some embodiments, three of the tissue anchors are connected with a tensioning member (5). In some embodiments, four of the tissue anchors are connected with a tensioning member (5). In some embodiments, five of the tissue anchors are connected with a tensioning member (5). In some embodiments, six of the tissue anchors are connected with a tensioning member (5). In other embodiments where more than six tissue anchors are deployed, more than six tissue anchors are connected with a tensioning member (5). In various embodiments, two, three, four, five, six, or more than six of the deployed tissue anchors are slidably connected with a tensioning member (5). And thus, when tensioning is applied to the tensioning member, the two, three, four, five, six, or more than six of the deployed tissue anchors are pulled towards one another and the distance between each pair of the tissue anchors is reduced.

Figure 1B:
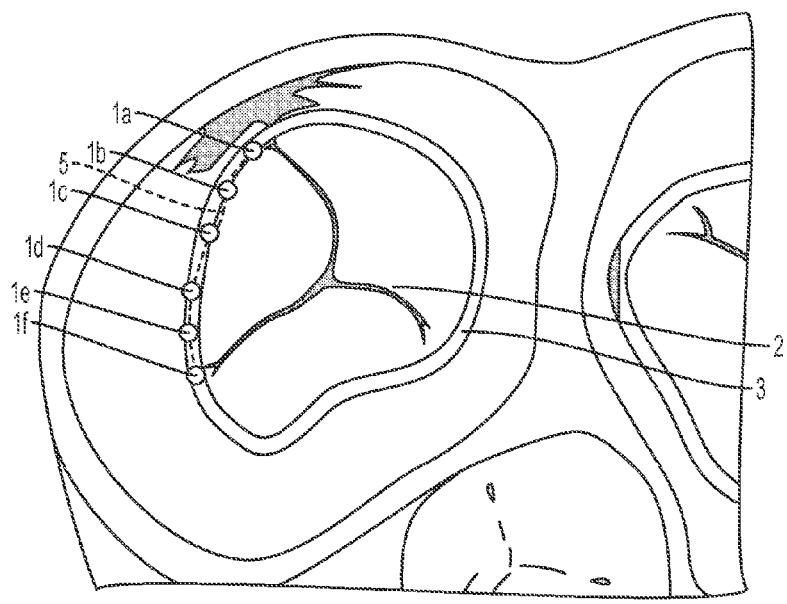

Upon reducing the distance among the six tissue anchors (1a-1f), the circumference of the tricuspid annulus is reduced, thereby effectively reducing the size of the tricuspid valve, as shown in FIG. 1B. In other words, reducing the circumference of the tricuspid annulus (3) and, thus, facilitating a coaptation of the tricuspid valve (2) leaflets and reduce or eliminate the tricuspid valve regurgitation jet. As a result, the tricuspid valve (2) can be fully closed during right ventricular systole.

One with ordinary skill in the art would understand that FIGS. 1A-1B illustrate certain embodiments of the present teachings and other locations can also be used for deploying tissue anchors and and/or other number of tissue anchors/fasteners can also be used to reduce the circumference of a tricuspid annulus.

According to some embodiments, all the tissue anchors (1a-1f) are positioned along the posterior annulus. According to other embodiments, all tissue anchors (1a-1f) are positioned along the anterior annulus. According to other embodiments, at least one tissue anchor (1a) is positioned on the posterior annulus and the other tissue anchors (1b-1f) are placed on the anterior annulus. In other embodiments, one or more tissue anchors are placed on the septal annulus. According to yet other embodiments, at least one tissue anchor (1a) is placed at a location at or close to the commissure of the posterior and septal leaflets and the other tissue anchors (1b-1e) are placed at locations between the commissure of the posterior and septal leaflets and the commissure of the posterior and anterior leaflets. According to yet other embodiments, one tissue anchor (1f) is placed at a location at or close to the commissure of the posterior and anterior leaflets. According to yet other embodiments, at least one tissue anchor (1a) is placed at a location at or close to the commissure of the anterior and septal leaflets and the other tissue anchors (1b-1e) are placed at locations between the commissure of the anterior and septal leaflets and the commissure of the posterior and anterior leaflets. According to yet other embodiments, one tissue anchor (1f) is placed at a location at or close to the commissure of the posterior and anterior leaflets.

According to some embodiments, two tissue anchors (1a and 1b) are deployed around the annulus circumference. According to other embodiments, more than two tissue anchors (for example, six tissue anchors 1a-1f) are deployed around the annulus circumference. In certain embodiments, three tissue anchors are deployed around the annulus circumference. In certain embodiments, four tissue anchors are deployed around the annulus circumference. In certain embodiments, five tissue anchors are deployed around the annulus circumference. In yet certain embodiments, more than six tissue anchors are deployed around the annulus circumference.

Additionally, according to some embodiments, tension is applied to all tissue anchors. According to other embodiments, tension is applied to some of the tissue anchors. In certain embodiments, tension is applied to two of the tissue anchors. In certain embodiments, tension is applied to three, four, five, six, or more than six of the tissue anchors.

Locating and Deploying Tissue Anchors

Another aspect of the present teachings relates to locating a first location on the tricuspid annulus. According to some embodiments, the first location is on the posterior annulus at or around the commissure of the posterior and septal leaflets. According to some embodiments, the first location is on the septal annulus at or around the commissure of the posterior and septal leaflets. According to some embodiments, the first location is on the posterior annulus at or around the commissure of the posterior and anterior leaflets. According to some embodiments, the first location is on the anterior annulus at or around the commissure of the posterior and anterior leaflets.

A further aspect of the present teachings provides various embodiments of placing a locating wire across the tricuspid annulus (3) at the first location. According to some embodiments, the wire crosses the tricuspid annulus (3) from the right atrium to the right ventricle (4). According to some embodiments, a wire of the present teachings crosses the tricuspid annulus (3) from the right ventricle to the right atrium (8).

A further aspect of the present teachings provides various embodiments of deploying a tissue anchor over the locating wire and across the tricuspid annulus. According to some embodiments, a portion of the tissue anchor is deployed inside the right ventricle (4). According to some embodiments, a portion of the tissue anchor (310a) is deployed inside the right atrium (8). According to some embodiments, the distal portion of the tissue anchor is deployed inside the right ventricle (4) and the proximal portion of the tissue anchor (310a) is deployed inside the right atrium (8). According to some embodiments, the distal portion of the tissue anchor (310a) is deployed inside the right atrium (8) and the proximal portion of the tissue anchor (310a) is deployed inside the right ventricle (4). Both distal and proximal portions of the first tissue anchor appose against each side of the annulus.

A further aspect of the present teachings provides various embodiments of locating a second location on the tricuspid annulus (3), placing a second locating wire across the tricuspid annulus (3), and then deploying a second tissue anchor across the tricuspid annulus. According to some embodiments, the second tissue anchor is adjacent to the first tissue anchor and at the posterior annulus. According to other embodiments, the second tissue anchor is adjacent to the first tissue anchor and at the anterior annulus. And according to some embodiments, the second tissue anchor is adjacent to the first tissue anchor and at the septal annulus. Also similarly, according to some embodiments, a portion of the second tissue anchor is deployed inside the right ventricle (4). According to some embodiments, a portion of the second tissue anchor (310a) is deployed inside the right atrium (8). According to some embodiments, the distal portion of the second tissue anchor is deployed inside the right ventricle (4) and the proximal portion of the tissue anchor (310a) is deployed inside the right atrium (8). According to some embodiments, the distal portion of the second tissue anchor (310a) is deployed inside the right atrium (8) and the proximal portion of the tissue anchor (310a) is deployed inside the right ventricle (4). Both distal and proximal portions of the second tissue anchor appose against each side of the annulus.

A further aspect of the present teachings provides various embodiments of reducing the circumference of the tricuspid annulus (3).

An exemplary method of the present teachings begins by percutaneously accessing the tricuspid annulus (3) from a suitable venous access site. According to some embodiments, the venous access site is located near the jugular vein, superiorly, from the femoral vein, inferiorly, or from other suitable sites.

Figure 2:
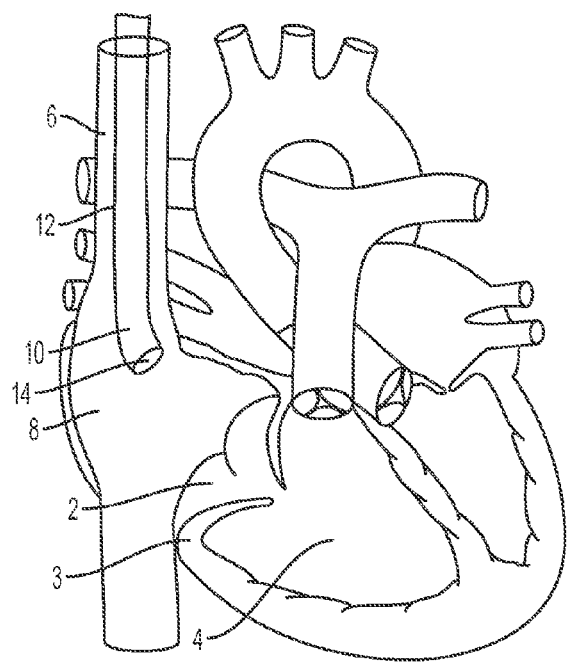
FIG. 2 is a perspective view of an exemplary guide percutaneously inserted into the right atrium in accordance with the present teachings.

According to some embodiments of the present teachings, as illustrated in FIG. 2, a suitable guide (12) is directed into the internal jugular vein, extends through the right brachiocephalic vein, and the superior vena cava (6), and reaches the right atrium (8). The distal end (10) of the guide (12) remains inside the right atrium (8). The proximal end (not shown) of the guide (12) remains outside of the body. The guide (12) has an axial lumen (14) extending from its proximal end through its entire length to its distal end (10). This axial lumen (14) of the guide (2) serves as a conduit, allowing one or more catheters be slidably disposed within and providing access to the right heart chambers. According to some embodiments, the guide (12) remains in place as illustrated in FIG. 2 during the entire procedure. According to some embodiments, the guide (12) is removed, for example, during the procedure when other suitable means, such as a locating wire, maintains such a percutaneous access.

According to some embodiments, the guide (12) is a 12 French (F) sheath. According to some embodiments, the guide (12) is a single lumen sheath that can accommodate all subsequent catheters to slide therein. Alternatively, in some embodiments, the guide (12) is a multi-lumen sheath. It would be appreciated by persons of ordinary skill in the art that the size and the exact configuration of the guide (12) is not limited to what is disclosed herein.

In various embodiments, a percutaneous repair of the tricuspid valve (2) starts with identifying and obtaining an access to a first location on the tricuspid annulus (3). FIGS. 3-7 illustrate some embodiments where a locating wire gains an access to the tricuspid valve (2) from the right ventricle (4) and is advanced across the tricuspid annulus (3) into the right atrium (8). Upon doing so, the distal end of the locating wire extends from the venous access site through the lumen (14) of the guide (12), reaches the right atrium (8), extends distally through the tricuspid valve (2), reaches the right ventricle (4), advances across the tricuspid valve (2) annulus, and extends proximally out of the body through the lumen (14) of the guide (12). As a result, both ends of the wire are outside of the body.

Figure 3A:
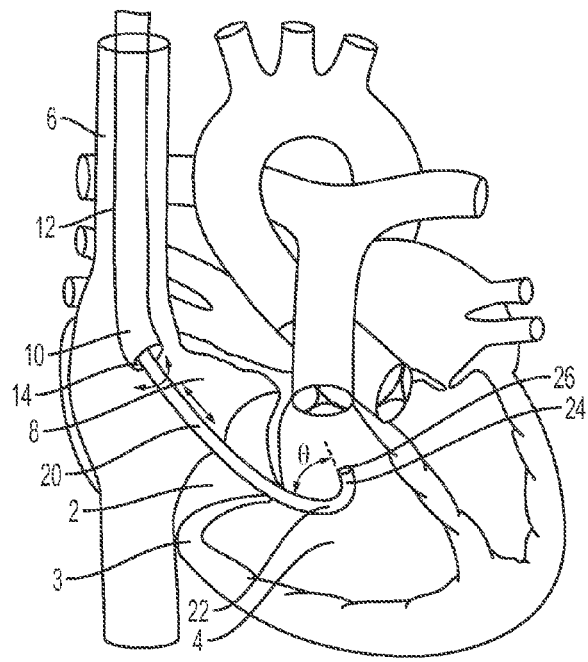
FIGS. 3A-3B are perspective views of an exemplary wire delivery catheter inserted into the right ventricle in accordance with the present teachings.

FIG. 3A illustrates an embodiment where a wire delivery catheter (20) is directed into the right ventricle (4). In one embodiment, a wire delivery catheter is inserted (20) from the proximal end of the guide (12) through the lumen (14) of the guide (12) and reaches the right atrium (8). As shown in FIG. 3A, as the distal end (24) of the wire delivery catheter (20) extends beyond the distal end (10) of the guide (12), the wire delivery catheter (20) is extended further distally through the opening among tricuspid valve (2) leaflets and reaches the right ventricle (4). Inside the right ventricle (4), the distal end portion (22) of the wire delivery catheter (20) bends radially away from the longitudinal axis of the wire delivery catheter (20) and assumes a curved profile. According to some embodiments, the curved profile of the distal end portion (22) of the wire delivery catheter (20) is in the shape of the letter "J," the letter "U," or any curvature between 90° to 270° as marked as "θ" in FIG. 3A.

According to some embodiments, the distal end portion (22) of the wire delivery catheter (20) has a preformed curve, such that as the distal end (24) of the wire delivery catheter leaves the constraint of the guide (12) and enters the right ventricle (4), the distal end portion (22) of the wire delivery catheter (20) resumes its curved profile. According to some other embodiments, the wire delivery catheter (20) has a deflectable distal end portion (22), which is actuated to form a curved profile. It will be appreciated that the various catheters disclosed herein may have distal portions that are steerable in various manners for accurate positioning purposes. For example, the distal end portion of the wire delivery catheter is movable into a desired hook-like position by a guiding cable embedded in the luminal wall of the catheter, which may be pulled to configure the distal end portion of catheter into the hooked shape as shown. In some embodiments, the catheters utilized herein include a unidirectional or bi-directional steering mechanism. A steering mechanism may be positioned within and/or on the devices. Typically, the steering mechanism may include a pull wire terminating at a flat spring or collar. The steering mechanism has a more flexible distal section compared to the proximal catheter tube body. When tension is placed on the pull wire, the catheter distal end is deflected into a curve, which allows the device to be manipulated accurately within a heart chamber. The pull wire may be wound, crimped, spot welded or soldered to the flat spring or collar (not shown) placed in the catheter end. This provides a stable point within the device for the pull wire to exert tensile force and thus steer the device. The more proximal portion of the catheter may be reinforced by incorporating a helically wound or braided wire therein to provide column support from which to better deflect the distal section. Alternatively, the steering mechanism may consist of a superelastic material having a desired three-dimensional geometric shape at its distal end and sufficient rigidity to impart this shape in the device. By retracting the preformed steering wire into the stiffer proximal section of the device, the distal end of the device straightens. Extending the preformed steering wire into the more flexible distal section of the device causes the distal section to assume the shape of the steering wire. Alternatively, a device with a curved section can incorporate a tube or rod that can be advanced through that section to straighten it. An additional feature that may be incorporated in the device is a preformed shape in the distal section of the device. The distal section may be pre-formed into a curve that biases the device to maximize tissue contact when the device is positioned into the appropriate heart chamber. This curve may consist of a single arc or a nonlinear geometry, such as an "S". A pre-shaped rod, hypotube, wire or coil, created from a memory elastic material such as nickel titanium or spring steel may be thermally formed into the desired geometry, and inserted into the distal section (including a separate lumen) of the device during manufacturing or advanced through a dedicated lumen while the device is positioned in the heart. The shaped wire may be attached to the distal tip of the device for those non-removable pre-shaped rods and secured to the handle of the device at its proximal end to provide a reinforcing structure throughout the entire length of the device. The device body may also or alternatively be thermally formed into a desired geometry.

According to some embodiments, the wire delivery catheter (20) can be extended distally, retracted proximally, or turned axially as shown by the double-headed arrows in FIG. 3A.

Figure 3B:
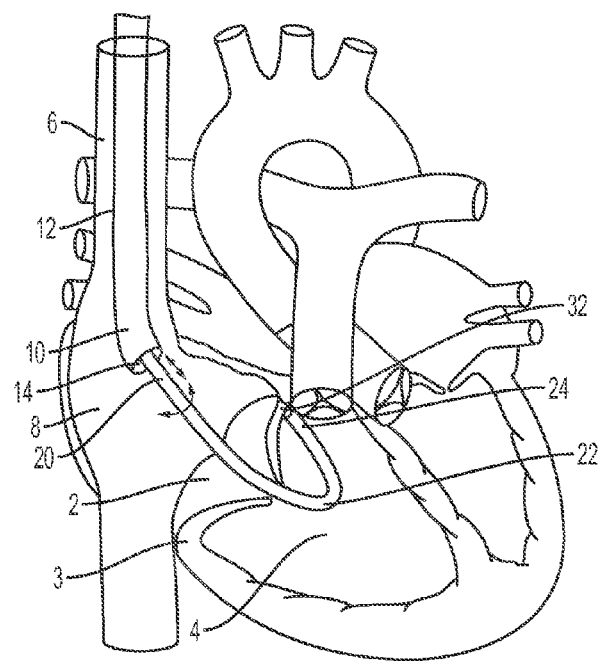

As further illustrated in FIG. 3B, the distal end (24) of the wire delivery catheter (20) is adapted to locate the first location (32) and then make contact with the tricuspid annulus (3) at the right ventricle (4) side.

Anatomically, the right coronary artery is approximately parallel to the circumference of the tricuspid valve (2). The anterior and septal leaflets lie approximately to the proximal half of the right coronary artery. The posterior leaflet of the tricuspid lies approximately to the distal half of the right coronary artery and between the middle of the right coronary artery and the transition of the distal right coronary artery to the posterior descending artery. The middle of the right coronary artery lies approximately next to the commissure of the anterior and posterior leaflets. The transition of the distal right coronary artery to the posterior descending artery, or the proximal posterior descending artery, lies approximately next to the commissure of the septal and posterior leaflets. One skilled in the art would understand that the anatomy of the heart may vary from a subject to another and the present teachings and the attached claims are not limited to the anatomy of any particular subject.

According to some embodiments, a first location (32) is identified by injecting a contrast dye inside the right coronary artery and the distal posterior descending artery. Alternatively, a location can be identified by advancing a radiopaque wire through the right coronary artery to the posterior descending artery. In various embodiments, the contrast dye and/or the radiopaque wire renders the right coronary artery visible under a radiographic imaging equipment such as X-ray, magnetic resonance, ultrasound, fluoroscope, or other imaging techniques. By visualizing the right coronary artery and the posterior descending artery, a location can be identified. Other methods of identifying a first location can also be used without exceeding the scope of the present teachings.

Upon identifying the first location (32), in various embodiments, a clinician steers the wire delivery catheter so that, as shown in FIG. 3B, the distal end (24) of the wire delivery catheter (20) aligns at the tricuspid annulus (3), extends upward at the interior of the right ventricle (4), and contacts the tricuspid annulus (3) at the first location (32). According to one embodiment, the first location (32) is at or near the commissure of the septal and posterior leaflets. Alternatively, the first location (32) is at or near the commissure of the anterior and posterior leaflets. One skilled in the art would understand that other locations along the tricuspid annulus (3) can also be used as a first location.

Figure 4A:
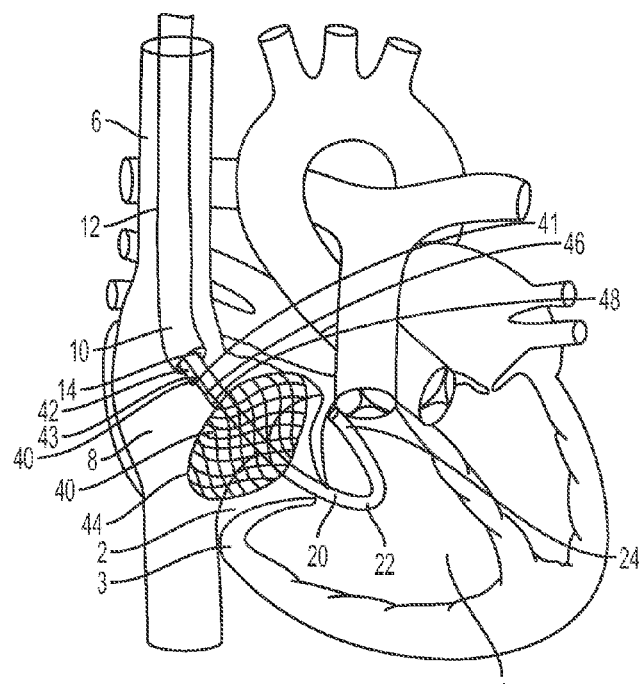
FIGS. 4A-4B are perspective views of an exemplary capture device deployed inside the right atrium in accordance with the present teachings.

In various embodiments, upon aligning the distal end (24) of the wire delivery catheter (20) at the location (32), a capture device (34) is deployed inside the right atrium (8). FIG. 4A illustrates an embodiment where a capture device (40) is advanced distally through the guide (12) and into the right atrium (8). According to some embodiments, a capture device (40) includes a sheath (42) and a capture basket (44). In some embodiments, a capture devices, such as the one illustrated in FIG. 4A, includes a capture basket (44) having an array of shape memory wire mesh on the distal end (48) of a rod (46). According to some embodiments, the capture basket (44) has a radially expanded basket-like profile for capturing the wire as described below and an elongated profile when being constrained within the sheath (42). In some embodiments, the capture basket (42) as shown in FIG. 4A is adapted to slide through the axial lumen (41) of the sheath (42), be pushed out of the distal end (43) of the sheath (42), and be retracted back from the distal end (43) of the sheath (42). In some embodiments, as the capture basket (44) extends outside of the distal end (43) of the sheath (42), it resumes its expanded profile. As the capture basket (44) is retracted back into the sheath (42), it collapses into its elongated profile. One skilled in the art would understand that the capture basket (44) can be used without the sheath (42), but with the guide (12) alone. Thus, what have been described herein should not be viewed as limiting.

In an exemplary use of the device, as illustrated in FIG. 4A, a capture device (40) having a capture basket (44) constrained to its elongated profile within the sheath (42) is directed through the lumen (14) of the guide (12). According to some embodiments, when a multi-lumen sheath is used as the guide, the capture device (40) extends through a separate lumen from the one used by the wire delivery catheter (20). According to other embodiments, when a single-lumen sheath is used as the guide, the capture device (40) extends side-by-side with the wire delivery catheter (20) through the same lumen of the guide. Once the distal end of the capture device (40) is advanced beyond the distal end (10) of the guide (12) and reaches the right atrium (8), the capture basket (44) is further pushed distally outside of the sheath (42) and, being free from the constraint of the sheath (42), the capture basket (44) deploys. In some embodiments, the deployed capture basket (44) can at least partially fill the volume of the right atrium (8).

Figure 4B:
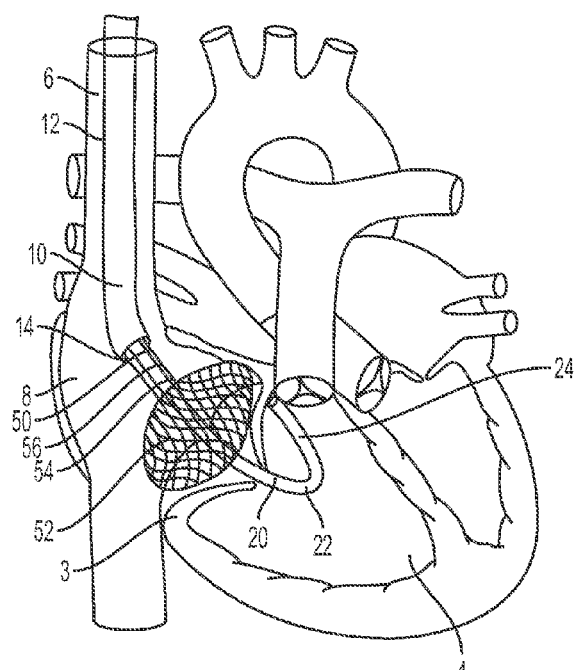

FIG. 4B illustrates another embodiment of the capture device (50). According to some embodiments, the capture device (50) includes a capture basket (52) at the distal end (54) of an elongated body (56). In some embodiments, the capture device (50), including the elongated body (56) and the capture basket (52) forming an axial lumen, is slidably disposed over the wire delivery catheter (20). Similar to the embodiment shown in FIG. 4A, this capture basket (52) is adapted to slide through the axial lumen (14) of the guide (12). Also similar to the embodiment shown in FIG. 4A, the capture basket (52) has an elongated profile when it is constrained within the lumen (14) of the guide (12) and a radially expanded basket-like profile when it is outside of the guide (12). Similarly, in some embodiments, the capture basket (52) can be made of an array of shape memory wire mesh.

According to some embodiments, this capture device (50) is adapted to slide over the wire delivery catheter (20), through the lumen (14) of the guide (12), and be pushed out of the distal end (10) of the guide (12). According to some embodiments, as the capture device (50) extends outside of the distal end (10) of the guide (12), it resumes its expanded profile. According to some embodiments, as the capture device (50) is retracted into the lumen (14) of the guide (12), it collapses into its elongated profile. According to some embodiments, the movement of the capture device (50) is independent of the movement of the wire delivery catheter (20). According to other embodiments, the movement of the capture device (50) is dependent to the movement of the wire delivery catheter (20). In certain embodiments, as the distal end (24) of the wire delivery catheter (20) contacts the annulus (3), the capture basket (52) is extended outside of the guide (12) and fully deployed inside the right atrium (8). Although certain embodiments of the capture basket (52) are shown in FIGS. 4A and 4B, one skilled in the art would understand that other capture devices can also be used without departing from the spirit of the present teachings. Thus, what is disclosed in present teachings should not be viewed as limiting.

Besides having a capture basket, according to other embodiments, a capture device includes a sheath with an expandable distal portion or a snare. One skilled in the art would understand that other types of suitable capture devices can also be used here. Thus what is disclosed herein and in FIGS. 4A-4B should not be considered as limiting.

Figure 5A:
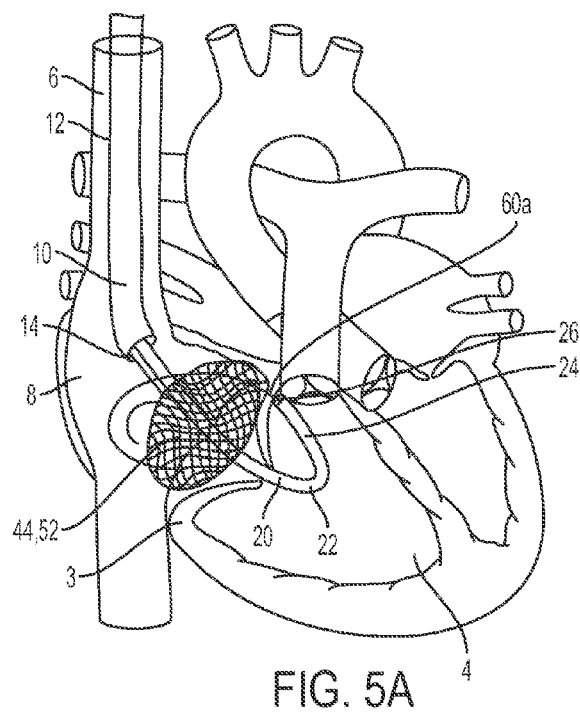
FIGS. 5A-5B are perspective views of an exemplary wire positioned across the annulus in accordance with the present teachings.

In various embodiments, with the capture basket deployed inside the right atrium (8) and the wire delivery catheter (20) properly positioned, a clinician can extend a locating wire (60*a*) across the tricuspid annulus (3). In some embodiments as illustrated in FIG. 5A, a wire is introduced through the wire delivery catheter (20). In these embodiment, the locating wire (60*a*) tracks through the axial lumen (26) of the delivery catheter (20), extends distally from its proximal end, contacts the tricuspid annulus (3), further extends and crosses the annulus (3) from the right ventricle (4) side, enters into the right atrium (8), and enters the space filled by the capture basket (44, 52). In some embodiments, the distal portion of the locating wire is captured by the capture basket.

According to some embodiments, as illustrated in FIG. 5A, the locating wire (60*a*) has a piercing tip which allows it to perforate the annulus (3). According to other embodiments, the locating wire (60*a*) has a radiofrequency (RF) energy delivery tip to assist its crossing of the tricuspid annulus (3). In these other embodiments, a suitable RF energy device (not shown) is coupled to the wire.

Figure 5B:
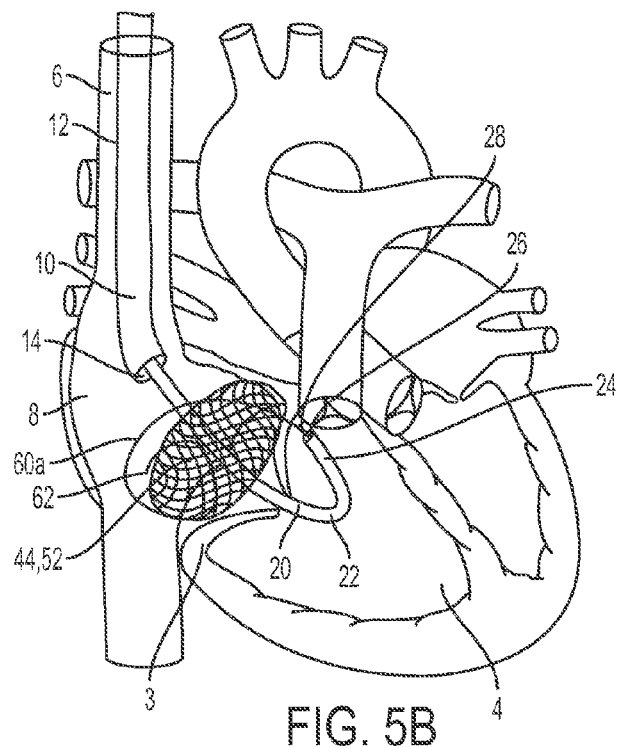

Yet according to other embodiments, as illustrated in FIG. 5B, the wire delivery catheter (20) also includes an extendable needle (28) that is capable of piercing the tricuspid annulus (3). In these embodiments, the locating wire (60*a*) tracks through the lumen (26) of the such wire delivery catheter (20), extends through the lumen of the extendable needle, alternatively, through the aperture created by the extendable needle (28) of the catheter (20), reaches into the right atrium (8), and enters into the space filled by the capture basket (44, 52). In some embodiments, the distal portion of the locating wire is captured by the capture basket (44, 52). One skilled in the art would understand that other methods and devices can also be used to access the right atrium (8). Thus, the particular examples described herein should be not viewed as limiting to the scope of the present teachings.

The various systems of the present teachings may also include different manners of ensuring that the catheter device(s) is/are properly position adjacent to tissue prior to use. For example, an impedance measurement device may be coupled to the perforating element itself, such as RF wire, or electrodes on the perforating element or on any separate element carried by the system. Such proximity determining devices may be used to confirm contact between the catheter device and the tissue surface by comparing the impedance between the electrode (such as RF wire) and a return path (indifferent patch electrode or second element electrode). When the electrode(s) only contact blood, the impedance is substantially higher than when the electrode element is in contact with the tissue surface. Each electrode is connected to a signal wire, with the signal wire connected to impedance measurement device. The signal wire may be connected to the impedance measurement device by way of a connector and cable system. The measurement device may be a power supply, a simple electrical resistance meter, or any other suitable device and method of use.

According to some embodiments, the distal portion (62) of the wire (60*a*) is designed to deflect or curl back to prevent inadvertent tissue damage. The ability to deflect or curl can be achieved by the geometrical construct of the wire (60*a*), such as a distal portion with a relatively smaller cross sectional profile (62); by the physical property of the material used in making the wire (60*a*), or by the shape memory property of the material used in making the wire (60*a*). Those skilled in the art would be able to incorporate known techniques and/or material to achieve this purpose without undue experimentation.

Figure 6:
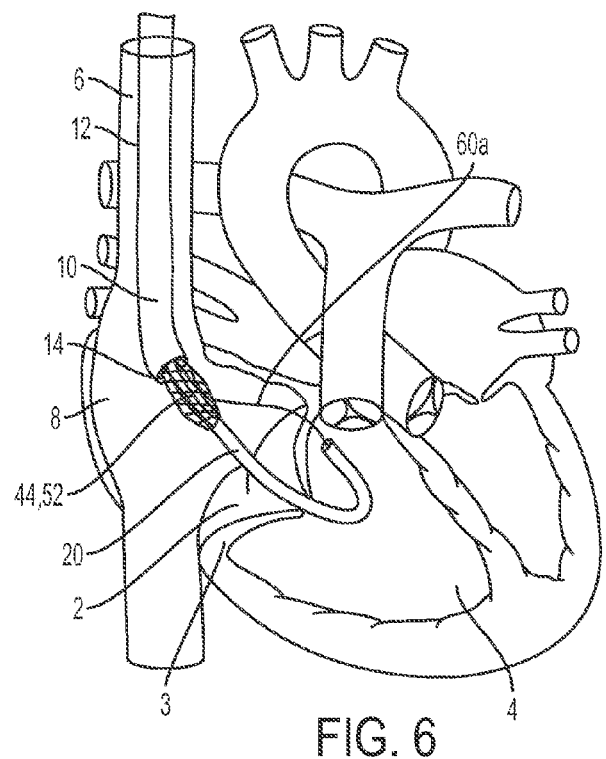
FIG. 6 is a perspective view of an exemplary wire captured and pulled through the guide in accordance with the present teachings.

Now referring to FIG. 6, as the distal portion of the locating wire enters the right atrium (8) and the space filled by the deployed capture basket (44, 52), it is captured by the capture basket (44, 52) of the capture device (40, 50). As a clinician retracts the capture basket (44) proximally back into the sheath (42) or into the guide (12), the capture basket (44, 52) collapses onto the distal portion of the wire (60*a*). As the clinician further retracts the capture device (40, 50) proximally, the capture device (40, 50) pulls the distal portion of the locating wire (60*a*) proximally through the lumen (14) of the guide (12) and out of the body.

Figure 7:
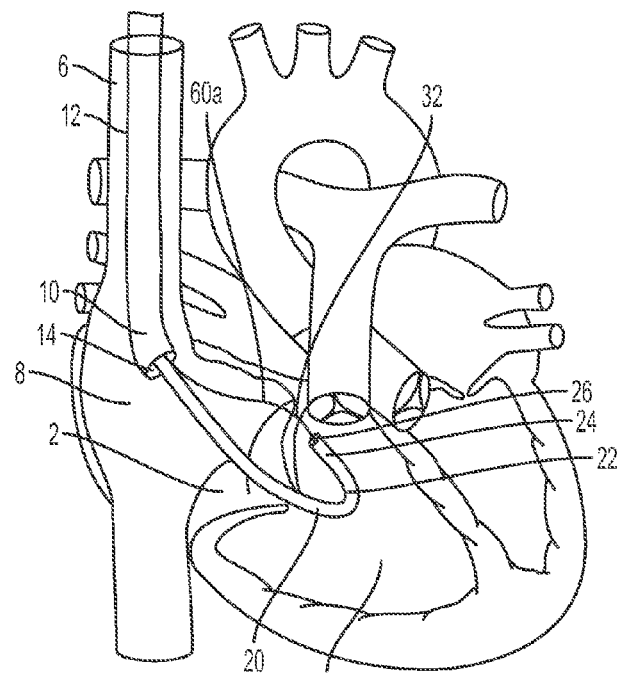
FIG. 7 is a perspective view of an exemplary wire positioned across the annulus in accordance with the present teachings.

In various embodiments, a clinician further retracts the capture device (40), including the sheath (42) and the capture basket (55) as shown in FIG. 4A or including the elongated member (56) with the capture basket (52) as shown in FIG. 4B, proximally through the lumen (14) of the guide (12) outside of the body. By doing this, in some embodiments, the clinician pulls the distal end of the locating wire (60*a*) outside of the body. As a result, as shown in FIG. 7, with one end of the locating wire (60*a*) remaining outside of the body, the other end extends from the venous excess site distally through the lumen (26) of the wire delivery catheter (20), passes the right atrium (8), the opening among the tricuspid valve (2) leaflets, and the right ventricle (4), crosses the tricuspid annulus (3) at a first location (32), extends proximally through the lumen (14) of the guide (12), and exits the venous access site. Thus, in many embodiments, with both the ends outside of the body, the wire (60*a*) maintains an access across the tricuspid annulus (3) at the first location (32) and facilitates the deployment of a tissue anchor as detailed below.

Figure 9A:
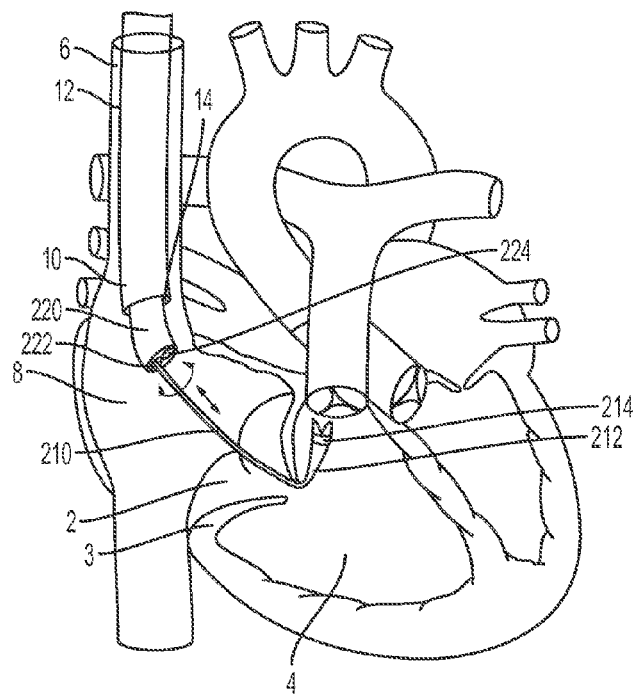
FIGS. 9A-9B are perspective views of exemplary locating devices inserted into the right ventricle in accordance with the present teachings.
Figure 9B:
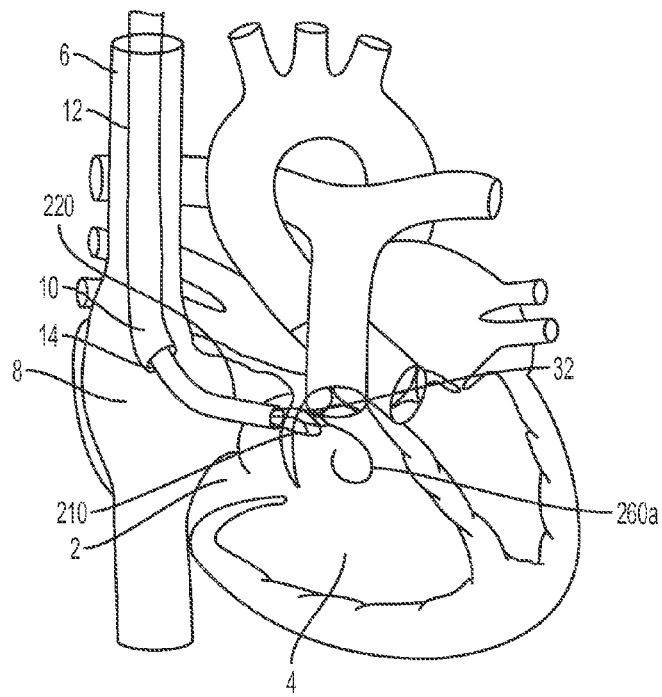
Figure 10:
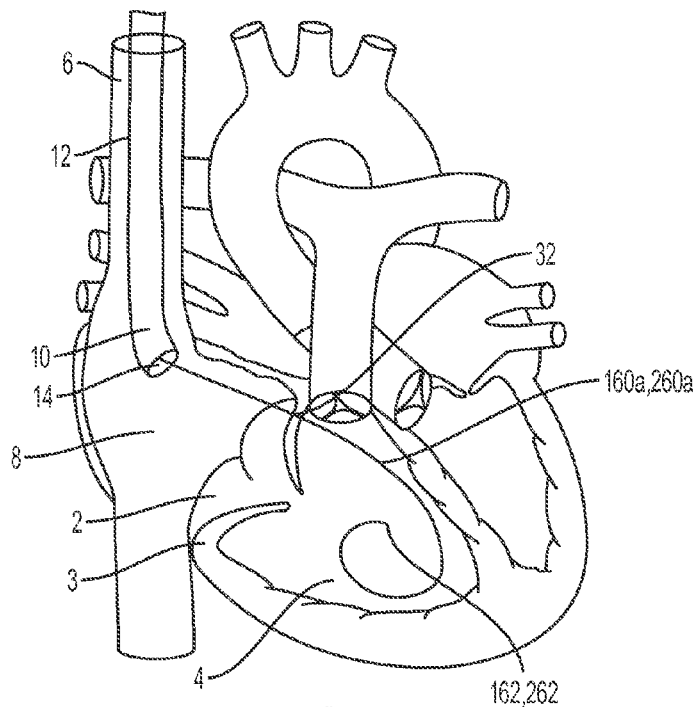
FIG. 10 is a perspective view of an exemplary wire positioned across the annulus in accordance with the present teachings.

FIGS. 8-10 illustrate some embodiments where the locating wire (160*a*) extends from the right atrium (8) across the tricuspid annulus (3) into the right ventricle (4) with the proximal end of the wire (160*a*) outside of the body and the distal end (162) of the wire (160*a*) inside the right ventricle. According to some embodiments, the locating wire is positioned at a first location with the aid of visualization tools such as fluoroscopy or echocardiography. According to other embodiments, the locating wire is placed at a first location across the annulus with the aid of a locating device, such as described herein.

Figure 8A:
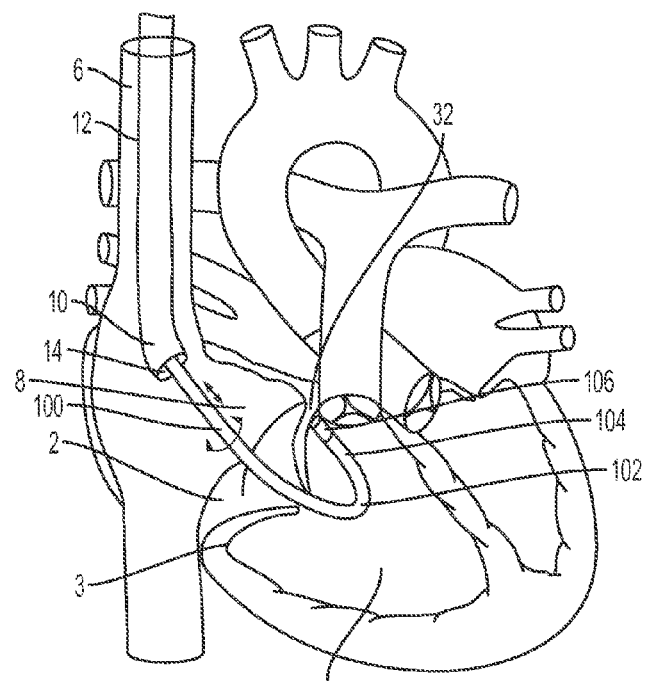
FIGS. 8A-8B are perspective views of an exemplary locating catheter inserted into the right ventricle in accordance with the present teachings.
Figure 8B:
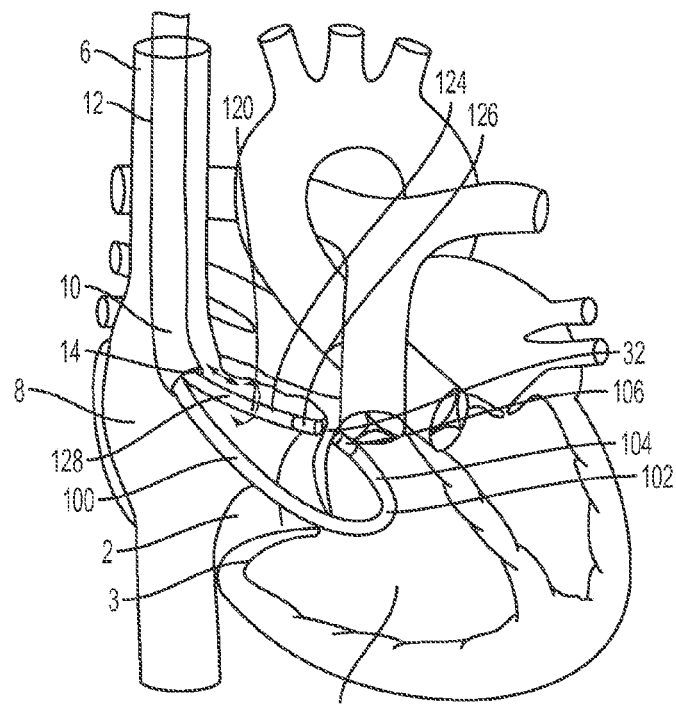
Figure 8C:
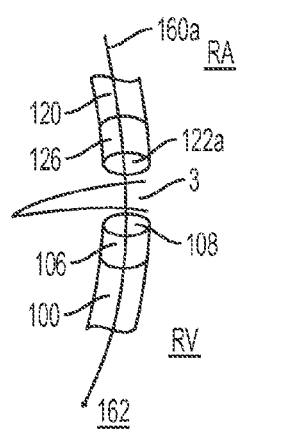
FIGS. 8C-8D are perspective views of exemplary wires across the annulus in accordance with the present teachings.

FIGS. 8A-8C illustrate various embodiments where the positioning of the wire delivery catheter (120) against the tricuspid annulus is guided by a locating catheter (100). According to some embodiments, the locating catheter (100) extends distally through the lumen (14) of the guide (12), through the opening among the tricuspid leaflets, and into the right ventricle (4). In certain embodiments, the locating catheter (100) enters into the right ventricle in a similar manner as the wire delivery catheter (20) described in accordance with FIGS. 3A and 3B. Following the same identification and placement processes as described herein, in various embodiments, the locating catheter (100) is positioned against the tricuspid annulus (3) at the first location (32) inside the right ventricle (4). According to some embodiments, the construct of the locating catheter (100) is similar to the wire delivery catheter (20) described above. In certain embodiments, the locating catheter has a preformed or an actuated curved distal end portion (102). In certain embodiments, the locating catheter is capable of extending distally and retracting proximally as indicated by the straight double-headed arrows in the FIG. 8A. In certain embodiments, the locating catheter is adapted to turn axially as indicated by the curved double-headed arrows in the FIG. 8A.

Continuing referring to FIG. 8A, in various embodiments, the locating catheter (100) has a magnet (106) at its distal end (104). In various embodiments, a wire delivery catheter (120) is advanced distally through the lumen (14) of the guide (12), reaching inside the right atrium (8), and approaching the tricuspid annulus (3). According to some embodiments, one of which is illustrated in FIG. 8B, the distal end (124) of the wire delivery catheter (120) includes a magnet (126). In various embodiments, the magnets (106, 126) on both the locating catheter (100) and the wire delivery catheter (120) have the opposite polarities. Thus, in some embodiments, as the wire delivery catheter (120) is approaching the tricuspid annulus (3), the magnet in the distal end of the wire delivery catheter is attracted by the magnet (106) on the distal end (104) of the locating catheter (100). In some embodiments, once the magnets (106, 126) lock up, the tricuspid annulus (3) is sandwiched between the distal ends (124, 102) of the two catheters as illustrated in FIG. 8B.

Figure 8D:
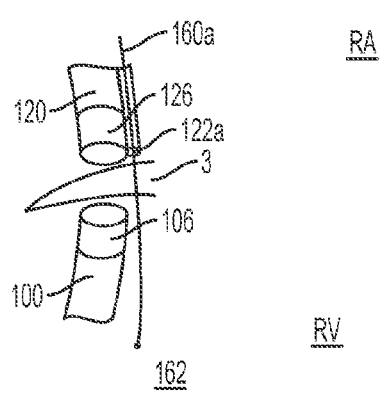

In various embodiments, a locating wire (160a) is then advanced from the right atrium (8) across the tricuspid annulus (3) into the right ventricle (4). According to some embodiments, as illustrated in FIG. 8C, the locating wire (160a) tracks along the axial lumen (122a) of the wire delivery catheter (120) and, upon crossing the tricuspid annulus (3). As the locating catheter (100) retracts proximally, the distal end (162) of the locating wire (160a) remains inside the right ventricle (4). According to other embodiments, as illustrated in FIG. 8D, the locating wire (160a) tracks along a side or off-centered axial lumen (122b) of the wire delivery catheter (120) and, upon crossing the tricuspid annulus (3), the distal end (162) of the locating wire (160a) enters the right ventricle (4). According to some embodiments, the wire delivery catheter (120) also has a deflectable distal end portion (128), which allows this distal end portion (128) deflect radially when the magnet (126) at the distal end (124) of the wire delivery catheter (120) is drawn to the location (32) by the magnet (106) at the distal end (104) of the locating catheter (100), as shown in FIG. 8B. Similarly, the wire delivery catheter (120) can be extended distally and retracted proximally or turned axially, as indicated by the double-headed arrows. According to some embodiments, the design or configuration of the locating wire (160a) is similar to what is described herein in according with FIGS. 5A and 5B.

FIGS. 9A and 9B illustrate yet certain other embodiments of the present teachings where a wire delivery catheter (220) is guided by a locating device (210). According to some embodiments, the wire delivery catheter (220) has two axial lumens (222, 224), one for a wire (260a) and the other for a locating device (210). The wire delivery catheter (220) enters the right atrium (8) through the lumen (14) of the guide (12). While maintaining the position of the wire delivery catheter (220) inside the right atrium (8), a clinician can extend the locating device (210) distally through the opening among the tricuspid valve (2) leaflets into the right ventricle (4) in a similar manner with respect to the wire delivery catheter (20) as described herein in accordance with FIGS. 3A and 3B. Similarly, the locating device (210) can have a curved distal portion (212), either preformed or actuated by a clinician, can be extended distally and retracted proximally, or be turned axially as indicated by the double-headed arrows in the FIG. 9A.

Upon entering the right ventricle (4), the distal end (214) of the locating device (210) is positioned at the first location (32) following the methods described herein in accordance with FIGS. 3A-3B, as well as FIG. 8B. Maintaining the position of the locating device (210), the wire delivery catheter (220) is pushed distally toward the tricuspid annulus (3) so that the annulus (3) is sandwiched between the distal end of the wire delivery catheter (220) and the distal end of the locating device (210), as shown in FIG. 9B. A locating wire (260a) is advanced distally from the wire lumen (224) across the tricuspid annulus (3) and into the right ventricle (4), as shown in FIG. 9B. According to some embodiments, the distal end (214) of the locating device (210) has openings or slots. In some embodiments, when the locating wire (260a) advances across the tricuspid annulus (3), it enters the openings or slots in the distal end (214) of the locating device (210). In other embodiments, the distal end (214) of the locating device (210) is configured that when a clinician retracts the locating device (210) proximally, the clinician would not disturb the locating wire (260a). According to some embodiments, the design and configuration of the locating wire (260a) is similar to what is described herein according to FIGS. 5A and 5B. One skilled in the art would understand that the particular embodiments in FIGS. 9A and 9B only illustrate certain aspects of the present teachings and that they should not be viewed as limiting the scope of the present teachings.

According to some embodiments, upon placing the locating wire (160, 260) across the first location (32) on the tricuspid annulus, the wire delivery catheter (120, 220), the locating catheter (100), and/or the locating device (210) are retracted proximally outside of the body. FIG. 10 illustrates various embodiments where the wire (160, 260) extends distally from a venous access site, tracks along the lumen of the wire delivery catheter (120, 220), enters into the right atrium (8), crosses the tricuspid annulus (3), and reaches the right ventricle (4). The proximal end of the locating wire (160, 260) remains outside of the body and is controlled by a clinician. The distal end (162, 262) of the locating wire (160, 260) remains inside the right ventricle (4). In some embodiments, the locating wire (160, 260) has a piercing tip which allows it to perforate the tricuspid annulus (3) or has a radiofrequency energy delivery tip which delivers a radiofrequency energy to the annulus tissue to perforate the tricuspid annulus (3). Additionally, similar to what is described herein according to FIGS. 5A and 5B, the distal portion of the locating wire is designed to deflect or curl back to prevent inadvertent tissue damage, as shown in FIG. 10.

With the locating wire (for example, 60a, 160a, or 260a in FIGS. 11-13) across the tricuspid annulus (3), in various embodiments, a tissue anchor (310a) is deployed at a location. According to some embodiments, as illustrated in FIGS. 11-13, a first tissue anchor delivery catheter (300) tracks along the locating wire (60a, 160a, 260a), across the tricuspid annulus (3), and into the right ventricle (4). In certain embodiments, the tissue anchor delivery catheter (300) is used to deliver a tissue anchor (310a) to the tricuspid annulus (3).

Figure 11A:
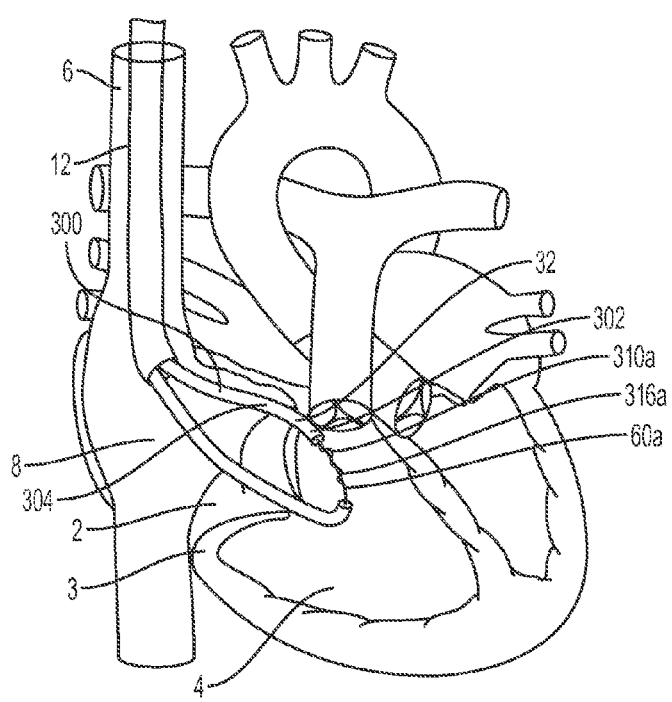
FIGS. 11A-11C are perspective views of an exemplary tissue anchor deployed across the tricuspid annulus in accordance with the present teachings.
Figure 11B:
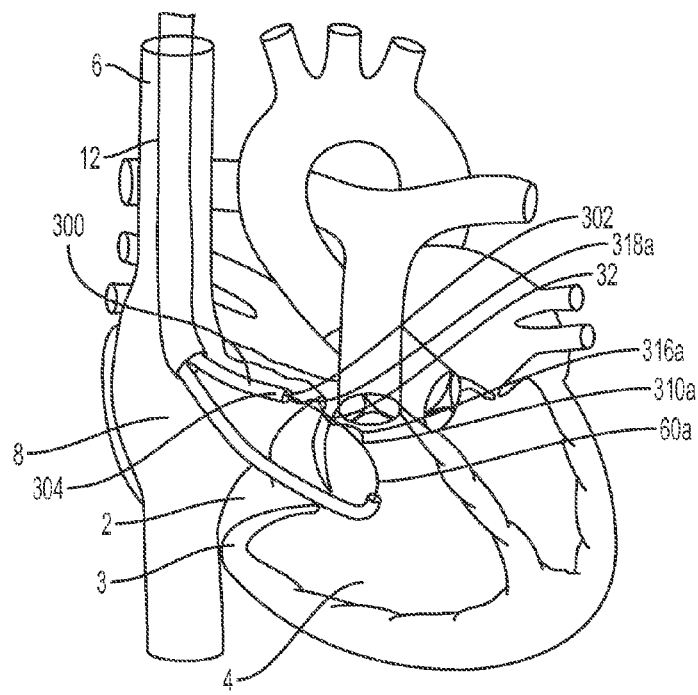
Figure 11C:
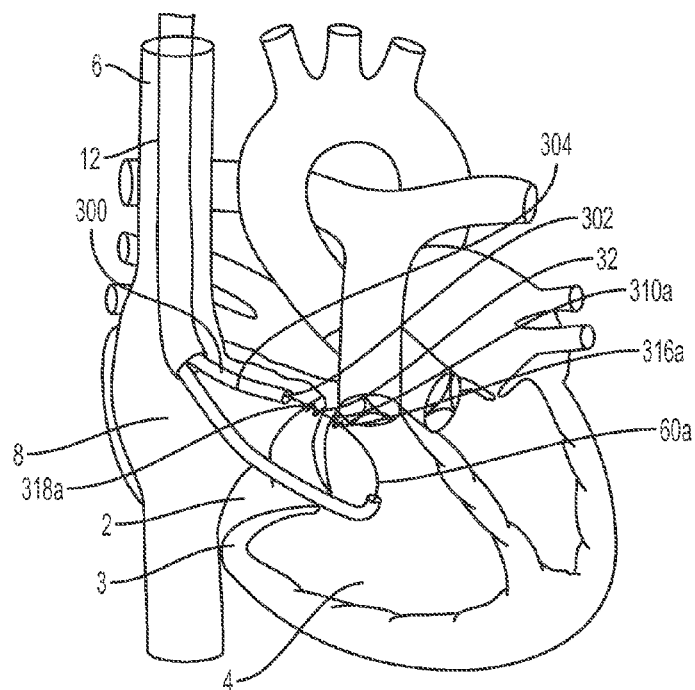
Figure 12A:
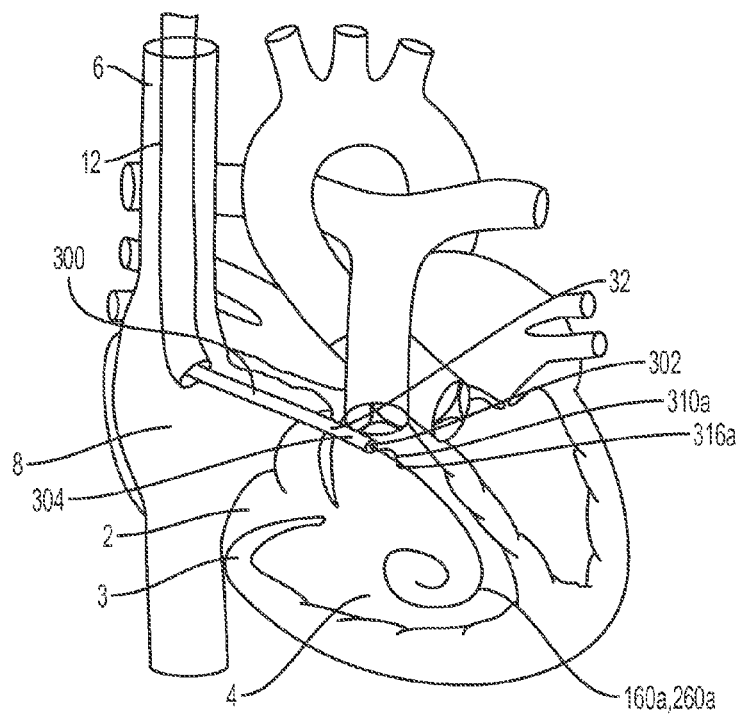
FIGS. 12A-12C are perspective views of an exemplary tissue anchor deployed across the tricuspid annulus in accordance with the present teachings.
Figure 12B:
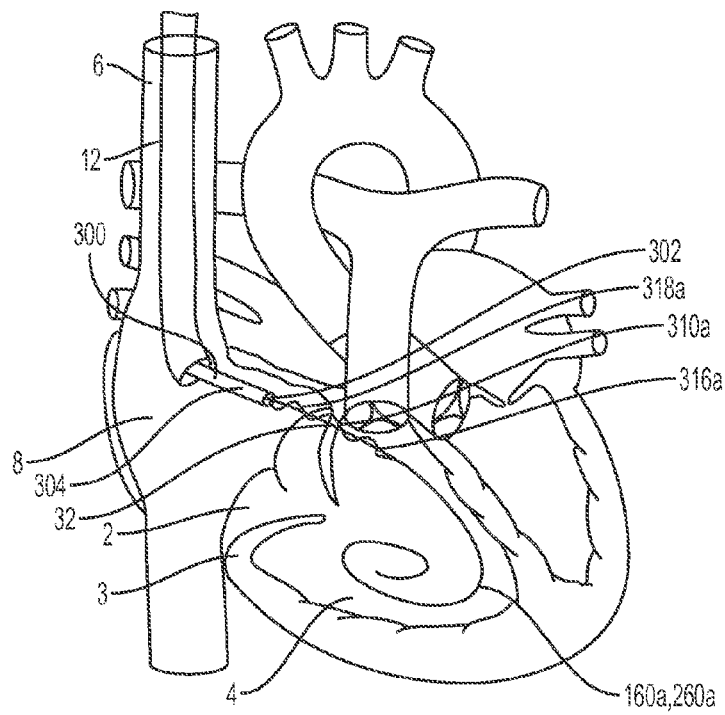
Figure 12C:
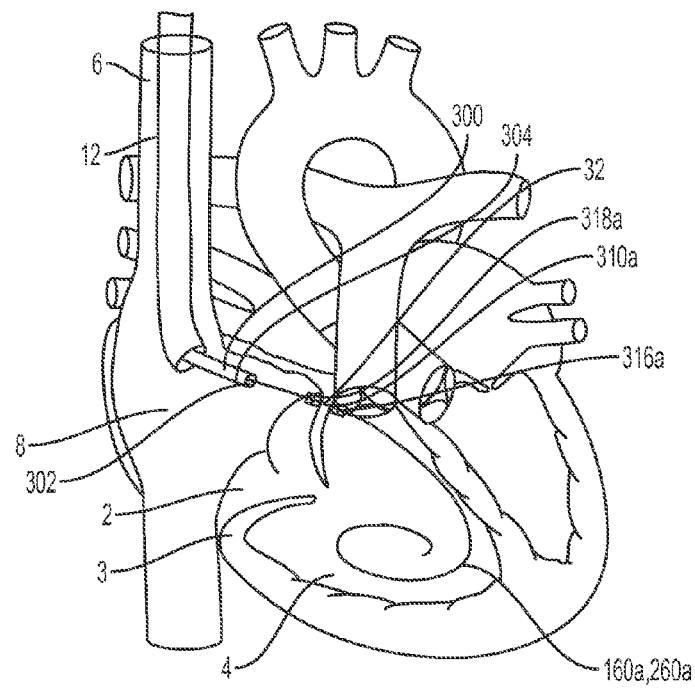

FIGS. 11-12 illustrate an exemplary delivery and deployment of a first tissue anchor (310a) across the tricuspid annulus (3). FIGS. 11A and 12A illustrate the process of exposing the distal portion (316a) of the tissue anchor (310a) and FIGS. 11B and 12 B illustrate the process of exposing the proximal portion (318a) of the tissue anchor (310a), according to the embodiments described in FIGS. 2-9. FIGS. 11C and 12C illustrate an exemplary deployment of the tissue anchor (310a) positioned at the location (32) according to the embodiment described in association with FIGS. 2-9.

Referring to FIGS. 11A and 12A, in some embodiments, a tissue anchor delivery catheter (300) holding a tissue anchor (310a) inside its longitudinal lumen (302) tracks along the wire (60a, 160a, 260a), across the tricuspid annulus (3), and into the right ventricle (4). Continuing referring to FIGS. 11A and 12A, in some embodiments, the tissue anchor (310a) is partially pushed distally outside of the distal end (304) of the tissue anchor delivery catheter (300). Once the distal portion (316a) of the tissue anchor (310a) or a sufficient amount of the anchor elements (316a, shown in FIGS. 11A and 12A) is exposed inside the right ventricle (4), a clinician stops pushing the tissue anchor (310a) distally and retracts the tissue anchor delivery catheter (300) proximally so that the distal end (304) of the tissue anchor delivery catheter (300) moves proximally across the annulus (3) and back into the right atrium (8). The clinician then exposes the proximal portion (318a) of the tissue anchor (310a) or the remainder of the anchor elements (312) of the tissue anchor (310a) within the right atrium (8) by further retracting the tissue anchor delivery catheter (300) proximally as shown in FIGS. 11B and 12B.

As illustrated in FIGS. 11C and 12C, in various embodiments, to deploy the tissue anchor (310a), the clinician pulls the proximal end of the tensioning member (314) such that the anchor elements (312) of the tissue anchor (310a) are drawn together against the opposite sides of the tricuspid annulus (3), thereby securing the first tissue anchor (310a) to the tricuspid annulus (3). As a result, as illustrated in FIGS. 11C and 12C, in some embodiments, the first tissue anchor (310a) is deployed across the tricuspid annulus (3) at the first location (32) with the distal portion (316) of the tissue anchor (310a) placed against the ventricular side of the tricuspid annulus (3), the proximal portion (318) of the tissue anchor (310a) placed against the atrial side of the tricuspid annulus (3), and the tensioning member (314) of the first tissue anchor (310a) extending proximally through the lumen (302) of the tissue anchor delivery catheter (300) to the outside of the body. According to some embodiments, the locating wire (60a, 160a, 260a) that marks the first location (32) and maintains the annulus access during the deployment of the first tissue anchor (310a) is withdrawn proximally once the distal portion of the tissue anchor delivery catheter crosses the annulus. In other embodiments, the locating wire (60a, 160a, 260a) that marks the first location (32) and maintains the annulus access during the deployment of the first tissue anchor (310a) is withdrawn proximally after the entire tissue anchor is deployed across the annulus. According to some embodiments, upon deployment of the tissue anchor across the annulus, the proximal end of the tensioning member (314) is controlled by the clinician from outside of the body.

Figure 13A:
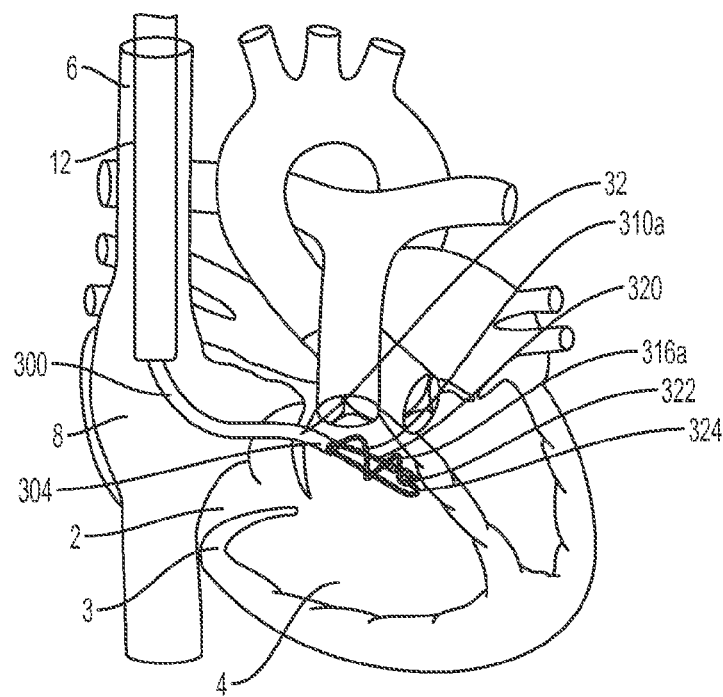
FIGS. 13A-13B are perspective views of an exemplary tissue anchor deployed across the tricuspid annulus in accordance with the present teachings.
Figure 13B:
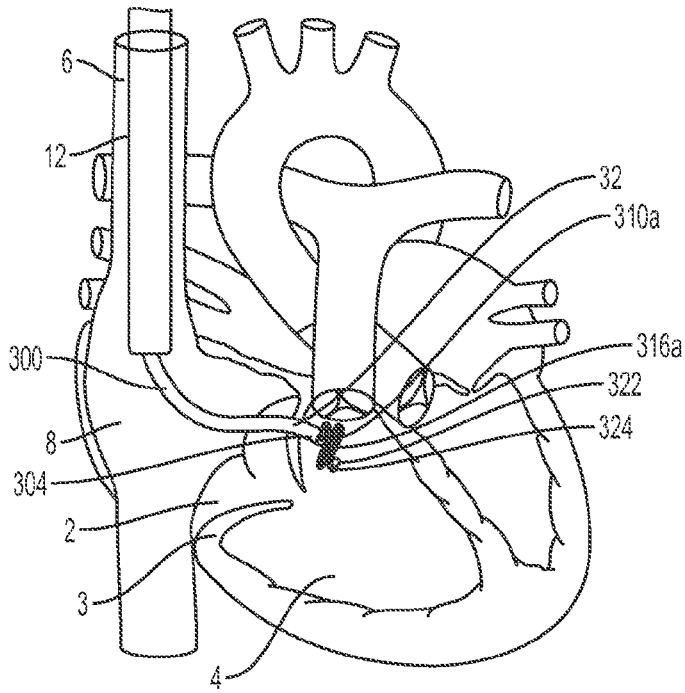

FIGS. 13A and 13B illustrate another embodiment of delivering and deploying the distal portion (316a) of a tissue anchor (310a) at the first location (32). Referring to FIG. 13A, in some embodiments, a tissue anchor delivery catheter (300) holding a tissue anchor (310a) and push wire (320) inside its longitudinal lumen (302) tracks along the wire (not shown), across the tricuspid annulus (3), and into the right ventricle (4). Continuing referring to FIG. 13A, in some embodiments, the tissue anchor (310a) is partially pushed distally outside of the distal end (304) of the tissue anchor delivery catheter (300) by the push wire (320). In this particular embodiment, tissue anchor (310a) includes tip (322). And continuing referring to FIG. 13A, a clinician stops pushing the tissue anchor (310a) and pulls the proximal end of a tensioning member (324) that is attached to the tissue anchor (310a). As a result, the tip (322) is drawn towards proximally and assists the tissue anchor (310a) to fold into itself, as shown in FIG. 13B. With the distal portion (316a) of tissue anchor (310a) in its deployed configuration, the clinician retracts the tissue anchor delivery catheter (300) proximally so that the distal end (304) of the tissue anchor delivery catheter (300) moves proximally across the annulus and back into the right atrium, exposes the proximal portion of the tissue anchor (310a), and deploys the proximal portion of the tissue anchor, all of which are similar to what are discussed in relation to FIGS. 11B, 11C, 12B, and 12C.

Persons with ordinary skill in the relevant art would understand that steps and sequences discussed in FIGS. 11A, 11B, 11C, 12A, 12B, 12C, 13A, and 13B are not required to be followed in order to practice the present teachings. In fact, any step discussed in FIGS. 11A, 11B, 11C, 12A, 12B, 12C, 13A, and 13B can be taken out of the sequence that includes that step and mixed with other sequences without traversing the scope of the present teachings. For example, the tissue anchor being partially deployed before the tissue anchor delivery catheter being retracted into the right atrium, as discussed in relation with FIGS. 13A and 13B, can be practiced in various embodiments discussed in FIGS. 11A-12C.

With the first tissue anchor (310a) securely deployed at the first location across the tricuspid annulus (3), the clinician can deploy a second tissue anchor (310b) at a second location (30) according to some embodiments of the present teachings. FIGS. 14-15 illustrate several exemplary deployment of a second tissue anchor (310b) at a second location (30) across the tricuspid annulus (3).

Figure 14A:
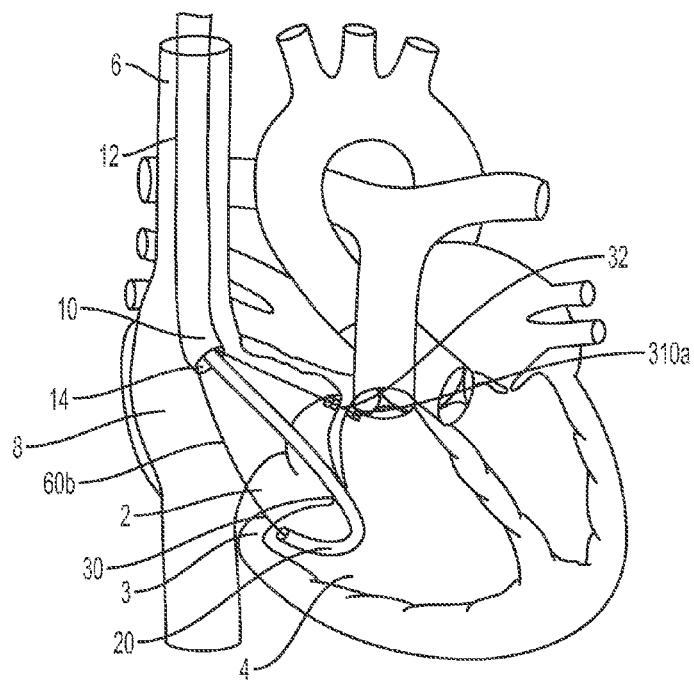
FIGS. 14A-14B are perspective views of an exemplary method where an exemplary second wire extends across the tricuspid annulus in accordance with the present teachings.

According to some embodiments, similar to what is described herein, for example, in FIGS. 3-7, a clinician uses the similar steps to position a wire delivery catheter (20) against the tricuspid annulus (3) from inside the right ventricle (4) at a second location (30). According to some embodiments, the positioning of the wire delivery catheter against the tricuspid annulus includes extending, retracting, turning, or otherwise manipulating the wire delivery catheter (20) to the second location (30) similar to the methods described herein or known to those with ordinary skill in the art. Similar to what is described herein in accordance with the FIGS. 3-7, one end of the second wire (60b) is advanced across the tricuspid annulus (3), captured by the capture basket (44, 52) as illustrated in FIGS. 4A and 4B, and pulled proximally through the lumen (14) of the guide (12) outside of the body. As illustrated in FIG. 14A, it results in that the wire (60b) is placed at the second location (30) and both the ends of the wire (60b) are outside of the body.

According to alternative embodiments, similar to what are described in FIGS. 8-10, a clinician takes similar steps to position the wire delivery catheter (120, 220) against the tricuspid annulus (3) from inside the right atrium (8) at a second location (30). According to some embodiments, this is done by extending, retracting, turning, or otherwise manipulating a locating catheter (100) or a locating device (210) at the second location (30) through methods similar to those described herein or known to those with ordinary skill in the art. Similar to what are described in accordance with FIGS. 8-10, the wire delivery catheter (120, 220) is positioned at the second location (30) through magnetic attraction or by the wire delivery catheter design discussed herein.

Figure 14B:
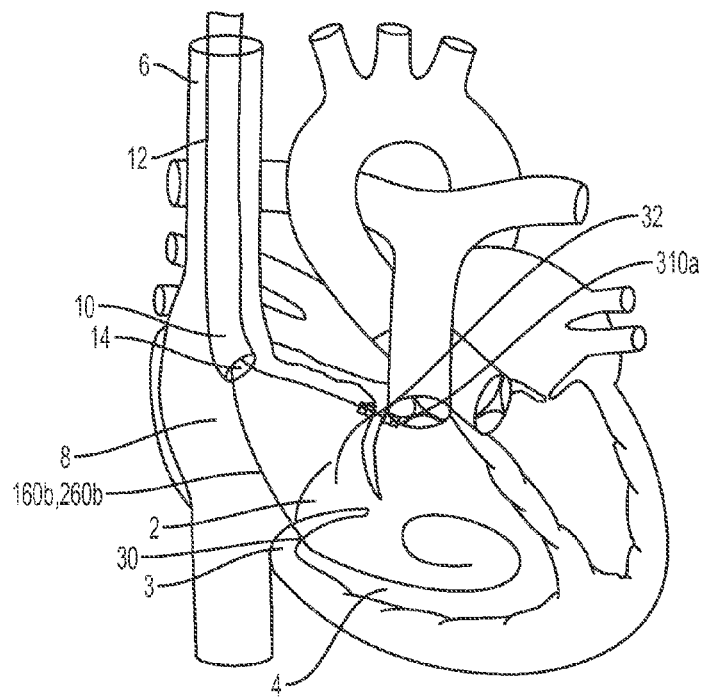

As illustrated in FIG. 14B, a second wire (160b, 260b) is advanced distally across the tricuspid annulus (3) and reaches the right ventricle (4) as described herein. The result is illustrated in FIG. 14B, where one end of the wire (160b, 260b) extends distally through the lumen (14) of the guide (12) and reaches the right ventricle (4). In other words, the distal end of the second wire (160b, 260b) resides inside the right ventricle (4) and the proximal end of the second wire (160b, 260b) resides outside of the body.

Figure 15A:
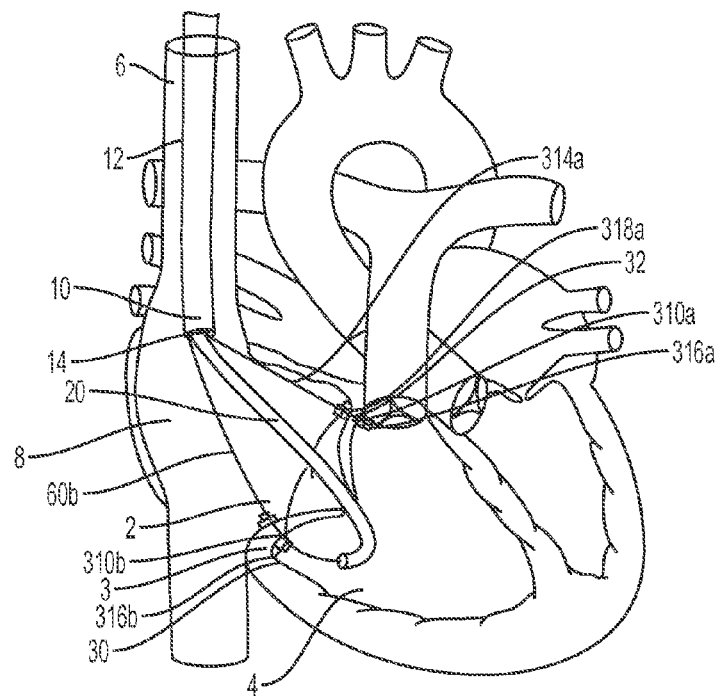
FIGS. 15A-15B are perspective views of an exemplary second tissue anchor deployed across the tricuspid annulus in accordance with the present teachings.
Figure 15B:
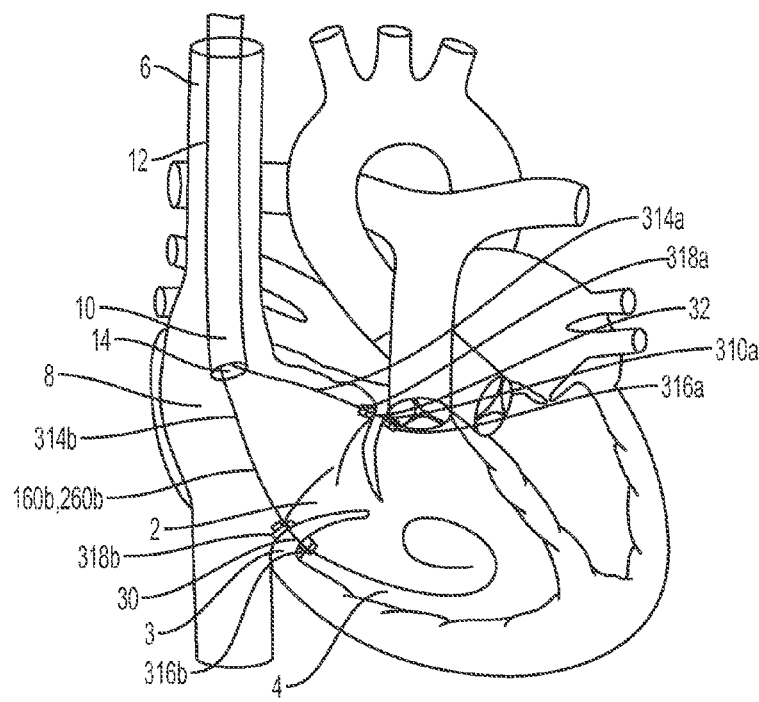

In various embodiments, a second tissue anchor (310b) is deployed at the second location (30) according to various embodiments described herein in accordance with FIGS. 15A-15B. FIGS. 15A and 15B illustrate the embodiments where the second tissue anchor (310b) is deployed across the tricuspid annulus (3) at the second location (30) with the distal portion (316b) of the second tissue anchor (310b) placed against the ventricle side of the annulus (3), the proximal portion (318b) of the tissue anchor (310b) placed against the atrial side of the annulus (3), and the tensioning member (314) of the second tissue anchor (310b) extending proximally through the venous access to the outside of the body. At this point, the second wire (60b, 160b, 260b) can be removed.

Figure 16:
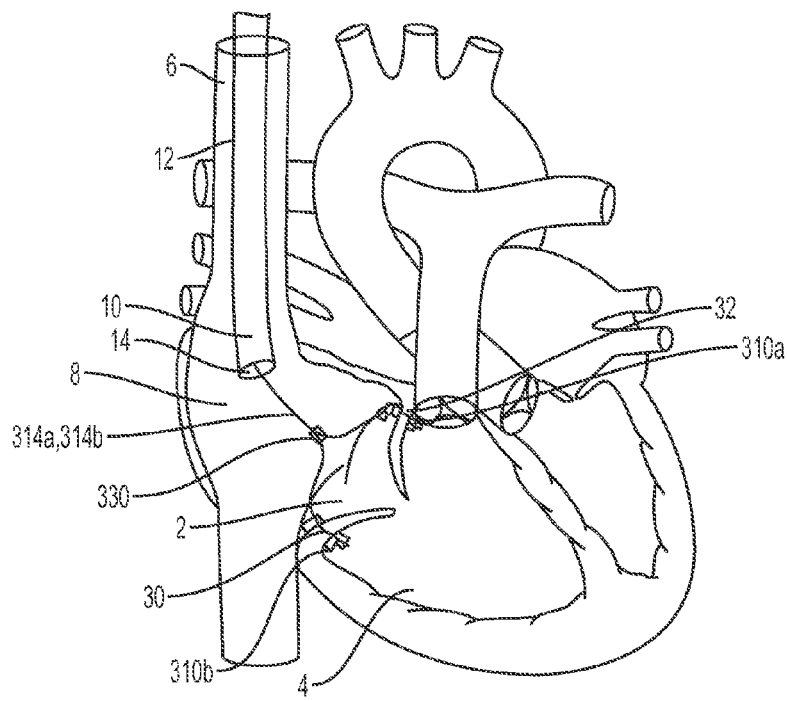
FIG. 16 is a perspective view of applying tension to two exemplary tissue anchor deployed across annulus in accordance with the present teachings.

FIG. 16 illustrates an exemplary reduction of a tricuspid valve (2). In various embodiments, the reduction is achieved by applying tension to two or more tissue anchors (310a and 310b) in FIG. 16. In some embodiments, the two or more tissue anchors (1a-1f in FIGS. 1A and 1B) are sequentially connected by a single tensioning member (5 in FIGS. 1A and 1B) (which is referred as "chain" or "chained"). And in these embodiments, the reduction is achieved by applying tension to the single tensioning member (5), which in turn pulls the two or more tissue anchors (1a-1f) closer to each other and plicates the tissue between each pair of the tissue anchors.

According to some embodiments, such as shown in FIG. 16, a tensioning member (330) connects a first tissue anchor (310a) at a first end of the tensioning member (330) and a second tissue anchor (310b) at a location next to the first end of the tensioning member. In some embodiments, the proximal end (not shown) of the tensioning member passes through the guide (12) and is located outside the body of the patient. In various embodiments, a clinician applies tension to the proximal end of the tensioning member (314a). In some embodiments, this tension pulls two tissue anchors (310a and 310b) closer to each other and thereby reducing the length of the tensioning member between the tissue anchors (310a, 310b), thereby plicating the tissue between the tissue anchors (310a, 310b) and reducing the circumference of the tricuspid annulus (3). In some embodiments, this tension, and the reduced distance between the two tissue anchors (310a, 310b), are maintained, for example, by a locker or other locking mechanisms. Although FIG. 16 shows that the two tissue anchors (310a, 310b) each is connected with a tensioning member and the two tensioning members are locked with a locker between the two tissue anchors (310a, 310b) after the tissue between the two tissue anchors is plicated, one with ordinary skill in the art would understand that these tissue anchors can be connected with one tensioning member, the one tensioning member can be used to plicate the tissue, and the locker is located at one side of the two tissue anchors (i.e., not between the tissue anchors). Suitable lockers include those well known in the art and those described in U.S. application Ser. No. 11/753,921, filed on May 25, 2007, entitled Lockers for Surgical Tensile Members and Methods of Using the Same to Secure Surgical Tensile Members, the disclosure of which is incorporated herein by reference. With the tensioning members (314a, 314b) are secured by a locker (not shown), the excess tensioning member (314a) proximal to the locker can be removed by a cutter, for example, a cutter disclosed in U.S. patent application Ser. No. 11/935,054, filed on Nov. 5, 2007, entitled Suture Cutter and Method of Cutting Suture, the disclosure of which is incorporated herein by reference. The guide (12) along with all the wire delivery catheters (20, 120, 220) and/or the tissue anchor delivery catheter (300) can then be retracted proximally and removed.

According to some embodiments, each tissue anchor is deployed sequentially. Specifically, the embodiments described in accordance with FIGS. 2-15 allow a clinician to place a wire (60, 160, 260) at the first location (32), followed by deploying a first tissue anchor (310a), and then place the same wire or a second wire at a second location (30), followed by deploying a second tissue anchor (310b).

According other embodiments, two or more locating wires are deployed simultaneously. Specifically, a bident catheter (400) can be used to place two wires at two locations at the same time. According to other embodiments, a catheter with more than two branches can be used to place multiple locating wires at multiple locations at the same time.

Figure 17:
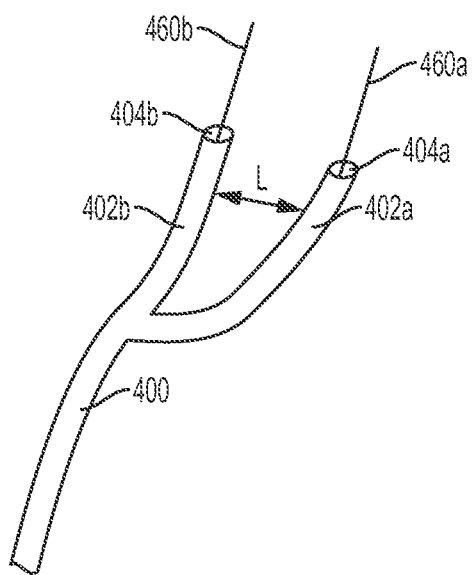
FIG. 17 is a perspective view of an exemplary bident catheter in accordance with the present teachings.

FIGS. 17-19 illustrate the use of a bident catheter (400) to place two wires (460a, 460b) across the tricuspid annulus (3). According to one embodiment, as illustrated in FIG. 17, a bident catheter (400) comprises a first catheter member (402a) having a first lumen (404a) for a first wire (460a) and a second catheter member (402b) having a second lumen (404b) for a second wire (460b). The first and second wires (460a, 460b) are slidably disposed within the first and second catheter lumens (404a, 404b), respectively. There is a pre-defined lateral distance "L" between the first catheter member (402a) and the second catheter member (402b).

Figure 18A:
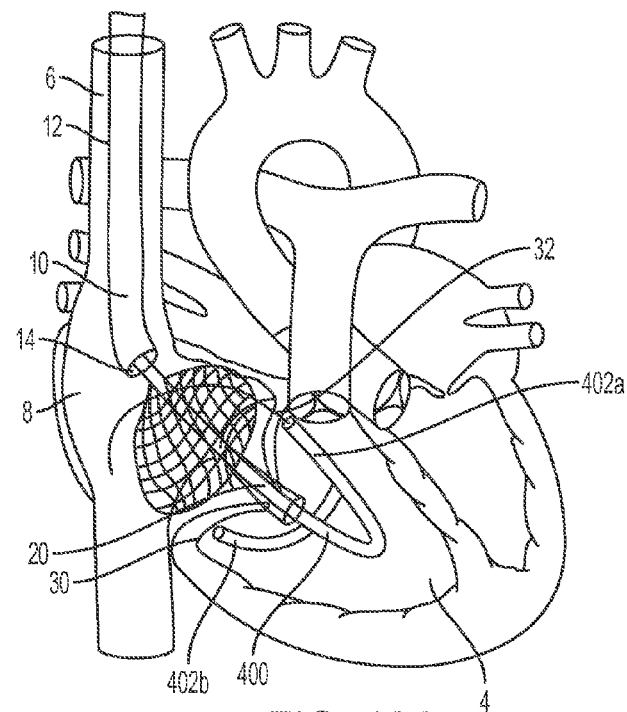
FIGS. 18A-18B are perspective views of an example of placing two exemplary wire across the tricuspid annulus with an exemplary bident catheter in accordance with the present teachings.

According to some embodiments, a bident catheter (400) is delivered to the right ventricle (4) and positioned against the tricuspid annulus (3) through a wire delivery catheter (20), as illustrated in FIG. 3A. According to some embodiments, similar to what are described herein in accordance with FIGS. 3-7, upon the wire delivery catheter (20) being positioned against the tricuspid annulus (3) from inside the right ventricle (4), the first wire (460a), extending through the lumen (404a) of the first catheter member (402a), is placed across the tricuspid annulus (3). The wire delivery catheter (20) is retracted proximally, exposing the second catheter member (402b) of the bident catheter (400), as illustrated in FIG. 18A. Once outside of the distal end (24) of the wire delivery catheter (20), the second catheter member (402b) expands laterally away from the first catheter member (402a) to a pre-defined distance. Without losing the placement of the first wire (460a), a clinician can turn the bident catheter (400) and/or the wire delivery catheter (20) so that the second catheter member (402b) is positioned at a second location (30). A second wire (460b) is then advanced across the tricuspid annulus (3) following the steps described herein and shown in FIGS. 4A-5B.

According to some embodiments, both the wires (460a, 460b) is captured by the capture device and the distal ends of the both wires (460a, 460b) are then withdrawn through the lumen (14) of the guide (12) outside of the body. As a result, as illustrated in FIG. 18B, two wires are placed at two locations, which can be used to facilitate the deployment of two tissue anchors (310a), following the steps discussed above and in accordance with FIGS. 11A-11C.

Figure 19A:
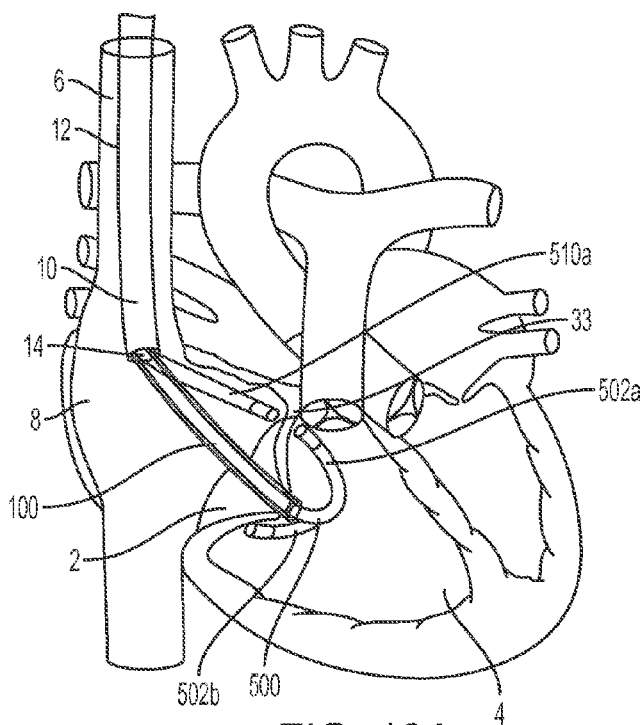
FIGS. 19A-19B are perspective views of an example of placing two exemplary wire across the tricuspid annulus with an exemplary bident catheter in accordance with the present teachings.

According to other embodiments as illustrated in FIG. 19A, a bident catheter or device (500) is delivered though the lumen of a locating catheter (100) to the right ventricle (4). As the distal end (104) of the locating catheter (100) is positioned against the annulus (3), a first catheter member (502a) is placed at a first location (32), attracting a first wire delivery catheter (510a) and facilitating the placement of a first wire (not shown). The locating catheter (100) is retracted proximally, exposing a second catheter member (502b) of the bident catheter (500) as illustrated in FIG. 19A. Once outside of the distal end (104) of the locating catheter (100), the second catheter member (502b) expands laterally away from the first catheter member (502a) to a pre-defined distance. Without losing the placement of the first wire delivery catheter (510a), a clinician can turn the bident catheter (500) and/or the locating catheter (100) so that the second catheter member (502b) is positioned at a second location (30). The second catheter member (502b) attracts the second wire delivery catheter (510b) and facilitates the placement of the second wire (not shown) across the tricuspid annulus (3) as shown in FIG. 19B.

According to some embodiments, the bident catheter are placed at two locations first and two wires are placed across the tricuspid annulus simultaneously or sequentially. Alternatively, in other embodiments, a first catheter member of a bident catheter is positioned at a first location first and a first wire is placed across the tricuspid annulus; and a second catheter member of the bident catheter is positioned at a second location and a second wire is placed across the tricuspid annulus.

Figure 18B:
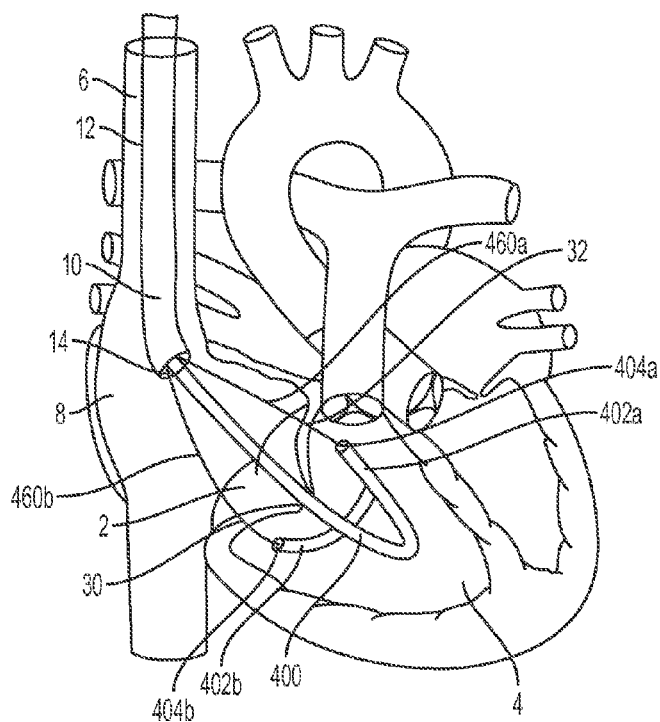
Figure 19B:
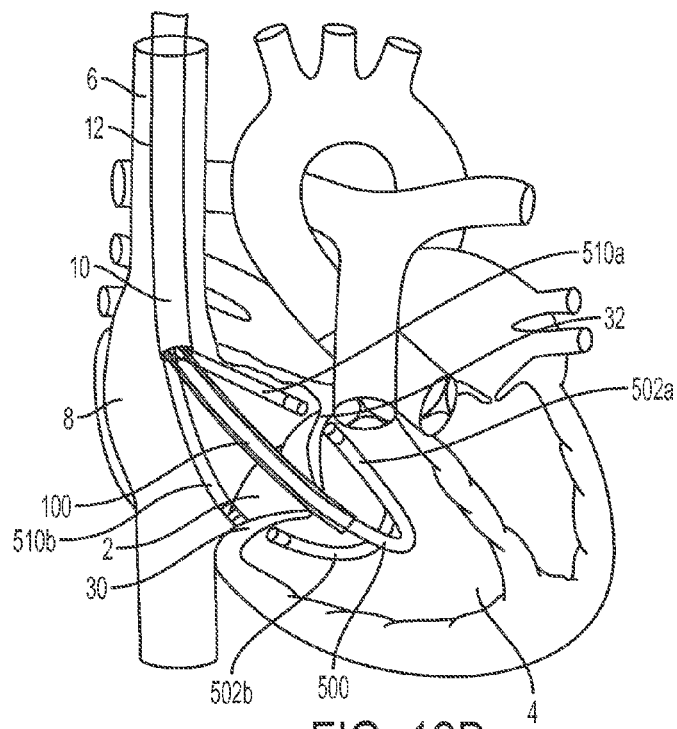

As a result, as illustrated in FIGS. 18B and 19B, two wires are placed at two locations, followed by the deployment of two tissue anchors according to the steps or steps similar with those discussed herein and in accordance with FIGS. 11-16.

Although an exemplary bident catheter is described above, one with ordinary skill in the art would understand that a three or more branched catheter can be used without departing from the spirit of the present teachings. The bident or multi-branched catheters described in conjunction with the drawings of the present teachings have some similarities to those in U.S. patent application Ser. No. 11/685,239, filed on Mar. 13, 2007, entitled Systems and Methods for Introducing Elements Into Tissue; U.S. patent application Ser. No. 11/685,240, filed on Mar. 13, 2007, entitled Tissue Anchors, Systems, and Methods, and Devices; U.S. patent application Ser. No. 11/685,242, filed on Mar. 13, 2007, entitled Devices and Methods For Introducing Elements into Tissue; and U.S. patent application Ser. No. 13/282,139, filed on Oct. 26, 2011, entitled Hand Operated Device for Controlled Deployment of a Tissue Anchor and Method of Using the Same; each of which is incorporated in its entirety by reference herein.

Tissue Anchors

Figure 20A:
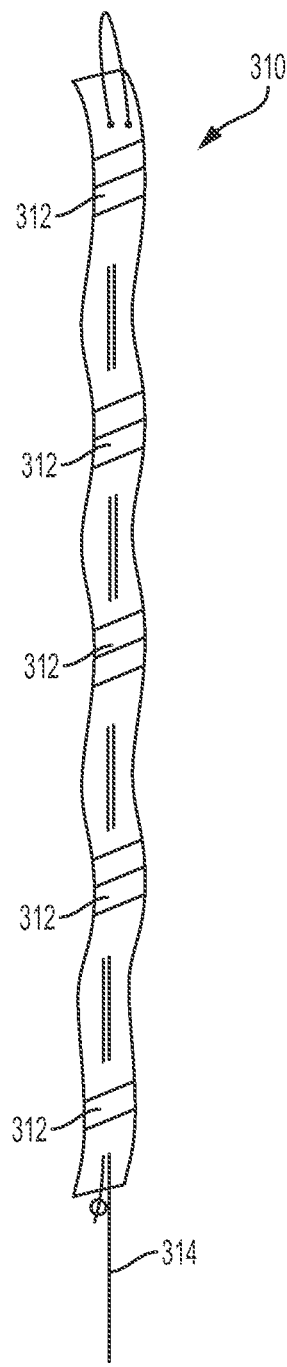
FIGS. 20A-20P are various exemplary tissue anchors in accordance with the present teachings.
Figure 21A:
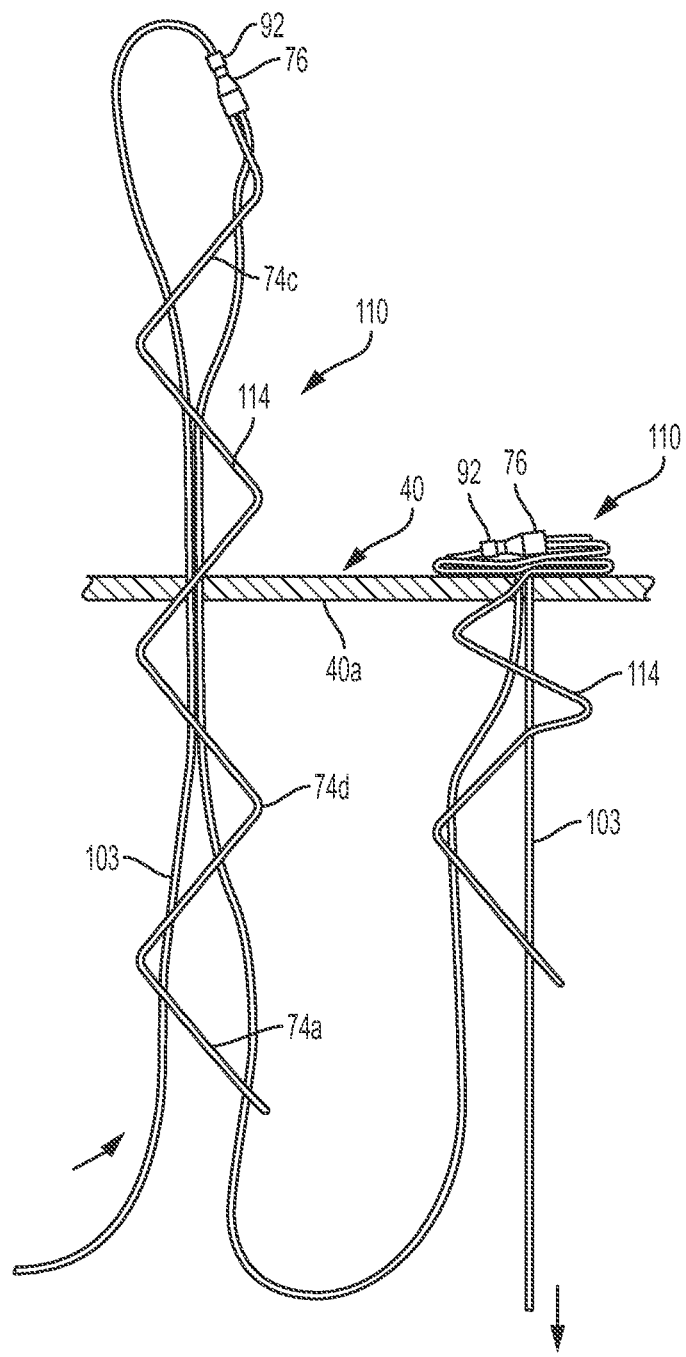
FIGS. 21A-21C are respective side elevational views illustrating an annuloplasty procedure in which two tissue anchors of an embodiment of the present teachings are tissue anchor chained together with a single tensioning member to plicate the tissue between the anchors in accordance with the present teachings.
Figure 21B:
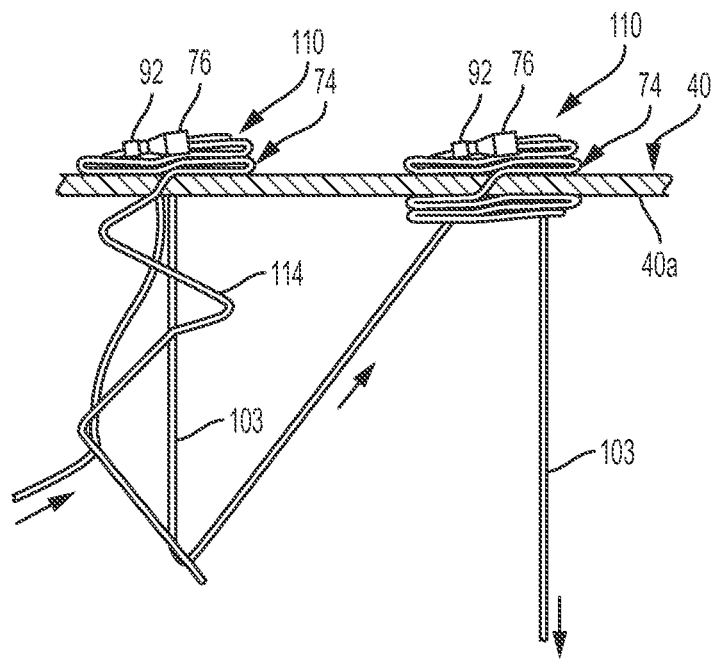
Figure 21C:
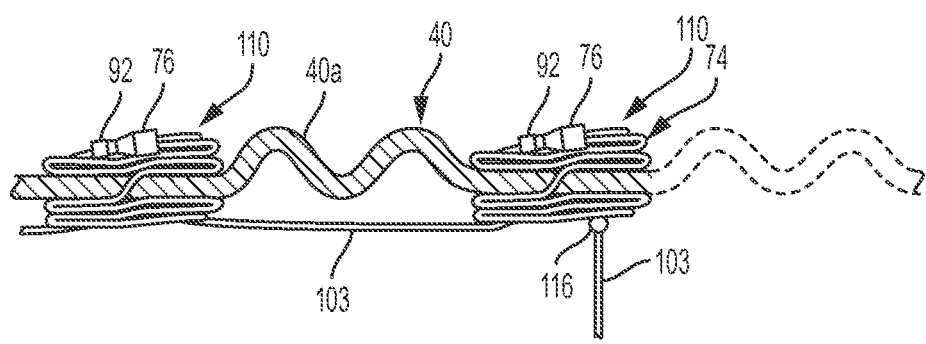

Another aspect of the present teachings relates to tissue anchors that can be used to reduce the circumference of a tricuspid valve (2). In general, any tissue anchoring devices known in the art can be used in a method of the present teachings. In various embodiments, the tissue anchor is collapsible. Referring to FIG. 20A, a tissue anchor (310a) includes a plurality of anchor elements (312) coupled with a tensioning member (314). The anchor elements (312) can be made from a surgical grade fabric material (e.g., a polyester material such as DACRON), in some instances, designed to promote tissue in-growth so that the anchors (310a) become at least in part encased in tissue over-time. The anchor elements (312) are coupled to a tensioning member (314), in this example, a suture, by threading the suture distally through the anchor elements (312) and proximally through the anchor elements (312). A slip knot or another type of locking mechanism is formed so that when a proximal end portion of the tensioning member (314) is pulled, all of the anchor elements (312) will be drawn together. In addition, the pulling of a proximal end portion of the tensioning member (314), in some embodiments, draws anchor elements at the distal end first and those at the proximal end later, as discussed elsewhere herein. Accordingly, in various embodiments, a tissue anchor of the present teachings includes an elongate or delivery configuration and a shortened or deployed configuration. In some embodiments, in the deployed configuration, the anchor elements are folded and leaves a long "tail" of the tensioning member, for example, a suture, leading from the anchor, for example, as shown in FIGS. 21A-21C. In some embodiments, the long "tail" can be used for subsequent attaching additional tissue anchors, tensioning, and plication, as described herein.

Figure 20B:
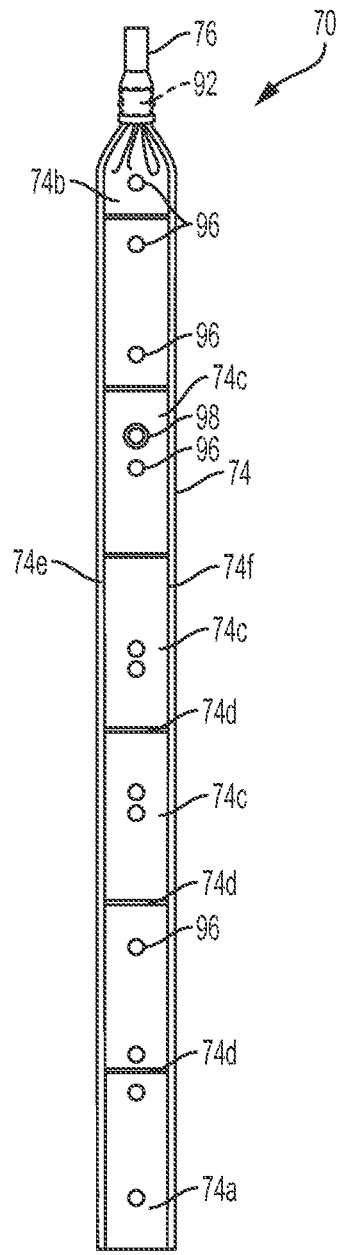
Figure 20C:
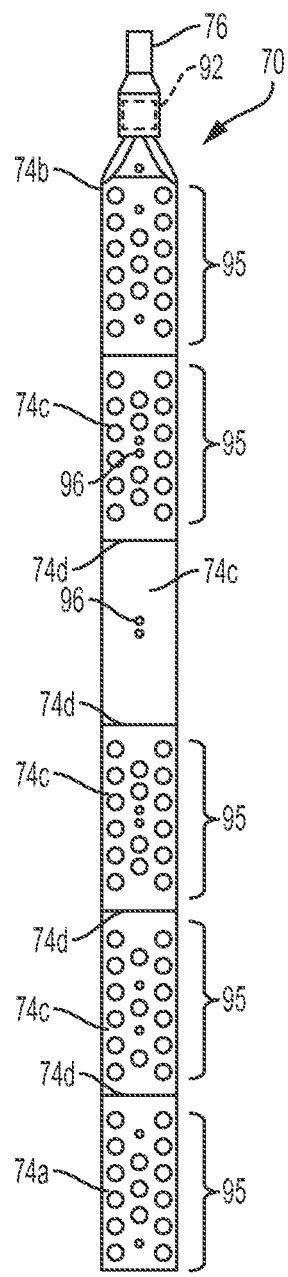
Figure 20D:
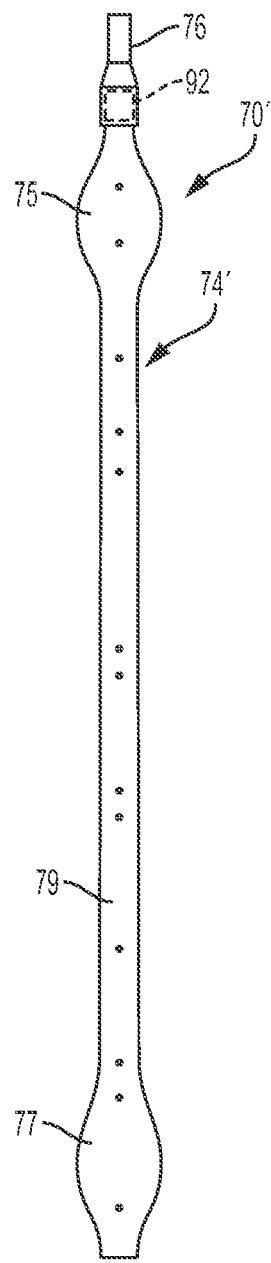

FIGS. 20B-20D show alternative tissue anchor devices. In various embodiments, a tensioning member (not shown) is used to activate an elongate strip (74) having proximal and distal end portions (74a, 74b). Strip 74 includes a tip (76) that is formed or otherwise secured on the distal end portion (74b). In some embodiments, the tensioning member and the tip (76) are arranged such that the tensioning member slides relative to the tip (76). In certain embodiments, the tensioning member can be threaded through the tip (76). As shown in FIGS. 20B-20D, tip (76) is made to be relatively rigid as compared to other flexible portions of strip (74) and of smaller diameter than the width of strip (74). In some embodiments, tip (76) helps to penetrate the annulus tissue as the inner tubular member (not shown) and the elongate strip (74) are extended through the tissue. A push wire, embodiments of which are described herein, may be used to push the tip (76) out of the tubular member at the desired time. In various embodiments, the tip (76) may protrude slightly from the inner tubular member as the tissue is penetrated to assist with piercing the tissue.

In some embodiments, the tip (76) may also assist with forcing distal portion or half (74b) of strip (74) into a folded or otherwise shortened configuration. To help prevent the distal portion (74b) of the elongate strip from pulling back through the tissue as the tissue anchor delivery catheter is withdrawn from the annulus tissue, in some embodiments, the free end of the tensioning member is pulled while the tissue anchor delivery catheter is still penetrated through the tissue and into the left atrium from the left ventricle, for example, as shown in FIG. 21A and also 13B. This forms the distal portion (74b) into a folded or otherwise shortened configuration. The inner tubular member may then be withdrawn without also withdrawing the elongate flexible strip (74) with it. In various embodiments, the proximal portion (74a) of the elongate strip (74) is then deployed by pulling the tissue anchor delivery catheter further in a proximal direction, and thereby exposing the full length of strip (74). The tensioning member is pulled or tensioned so as to draw and compress the proximal portion (74a) of the elongate strip (74) into a folded, shortened condition against an underside of the annulus tissue, for example, as shown in FIG. 21B.

As further shown in FIGS. 20B and 20C, the tensioning member or suture (not shown) can advantageously extend through respective fold portions (74c) of the elongate strip (74) in essentially an hourglass configuration. Specifically, thus, in some embodiments, adjacent portions of the suture located near the proximal and distal end portions (74a and 74b) of the strip (74) are spaced farther apart than the adjacent portions of the suture in the middle of the strip (74).

As further shown in FIG. 20C, radiopaque markers, such as distinct areas of dots (95), may be used for enabling the surgeon to visualize the folds of the elongate strip (74) during deployment and securement of the elongate strip (74). These dots or other radiopaque markers may be printed on the strip (74). For example, dots (95) or other markers may be formed with a platinum powder base ink or other suitable material that is radiopaque and biologically compatible. This radiopaque material may also add stiffness to the fold sections (74c) thereby helping to maintain the fold sections (74c) flat and increasing retention force on the tissue. Meanwhile, the fold lines (74d) between fold sections (74c) can remain highly flexible to create tight radius fold lines. As further shown in FIG. 20B, each of the holes (96) that the tensioning member or suture (72) is received through may be marked by circles (98) surrounding each hole (96) or other markers for visualizing purposes during assembly of the tensioning member or suture (72) with the elongate strip (74). Optionally, holes (96) may be eliminated and the suture may be threaded with a needle through the strip (74). One could also, for example, choose different sets of holes (96) along strip (74) for receiving the tensioning member or suture (72) thereby changing the width of the folds and/or number of folds and/or shape of the folds depending on the application needs or desires of the surgeon.

The tensioning member or suture (314 in FIG. 20A) may be threaded or otherwise attached along the strip (74) in any number of manners including, for example, x-patterns or other crossing patterns, zig-zag patterns, etc. that may alter the folded or otherwise shortened or compressed footprint of the anchor into various beneficial shapes, such as flower shapes, circular shapes or other rounded shapes, ball shapes or other configurations. Modifications of the manner in which the tensioning member or suture is threaded or otherwise attached along the length of strip (74) may result in higher or lower tensioning force being required to compress the anchor and/or higher or lower friction holding force that may help maintain the anchor in the compressed or shortened configuration.

The width of the elongate strip (74') may be varied along its length, such as by tapering, stepping, or forming an hourglass shape or shapes along the length of the strip (74). For example, as illustrated in FIG. 20D, having proximal and distal end portions (75, 77) of wider dimension than an intermediate or middle portion or portions (79) along the length of strip (74') will allow these wider portions (75, 77) may cover over the more intermediate folded portions (79) and prevent unnecessary contact with adjacent tissue during use. It will be appreciated that like reference numerals are used herein to refer to like elements in all embodiments and reference numerals with prime marks (') or double prime marks (") refer to like elements that have been modified in a manner as described herein or otherwise shown in the associated figure.

Strip (74) may have variable stiffness including, for example, a relatively rigid perimeter or relatively rigid edges (74e, 74f) (FIG. 20B) or intermittent relatively rigid sections (not shown) separated by flexible sections such as living hinges (not shown) that may aid in folding and securing the elongate strip into a folded condition.

Examples of a tissue anchor (310) described in conjunction with the above drawings of the present teachings have some similarities to those in U.S. patent application Ser. No. 12/273,670, filed on Nov. 19, 2008, entitled Tissue Anchor and Anchoring System, U.S. patent application Ser. No. 11/174,951, filed on Jul. 5, 2005, entitled Tissue Anchor, Anchoring System and Methods of Using the Same, U.S. patent application Ser. No. 13/777,042, filed on Feb. 26, 2013, entitled Tissue Anchor and Anchoring System, each of which is incorporated by reference herein in its entirety.

Other suitable tissue anchors can also be used. Examples of suitable tissue anchors include, but not be limited to, tissue fasteners, tissue pledgets, or tissue staples etc.

FIGS. 20E and 20F illustrate one alternative tissue anchor or fastener (550) usable with the various systems of the present teachings. Such a tissue anchor or fastener (550) may be rigid and coupled to a flexible tensioning member (552) or coupled such that the tissue anchor or fastener (550) slides along the flexible tensioning member (552), as necessitated by the fastening system in which the tissue anchor or fastener (550) is being used.

FIG. 20G is a side elevational view of an alternative tissue anchor or fastener (560) which is similar to that shown in FIGS. 20E and 20F, except that the tissue anchor or fastener (560) has a curved outer profile. The convex surface (562) of the curved outer profile is adapted to engage tissue and cause less trauma to the tissue than the flat profile shown in FIGS. 20E and 20F.

FIGS. 20H-20J illustrate another alternative tissue anchor or fastener (570) useful in the various systems and methods of the present teachings. This tissue anchor or fastener (570) includes two radially expandable portions (572, 574) which may be delivered through a catheter (576) in their nonexpanded state shown in FIG. 20H, and then expanded on opposite sides of the tissue (40) to trap the tissue (40) therebetween, as shown in FIGS. 20I and 29J.

Figure 20K:
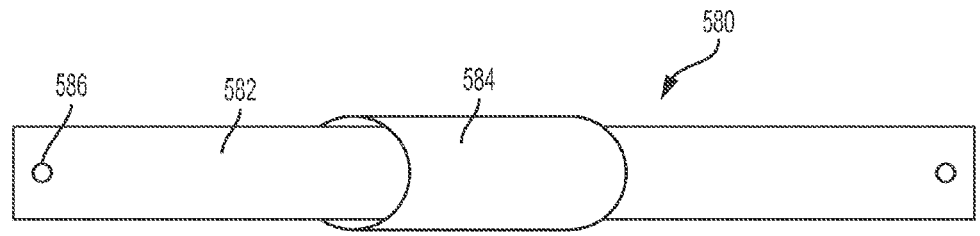
Figure 20L:
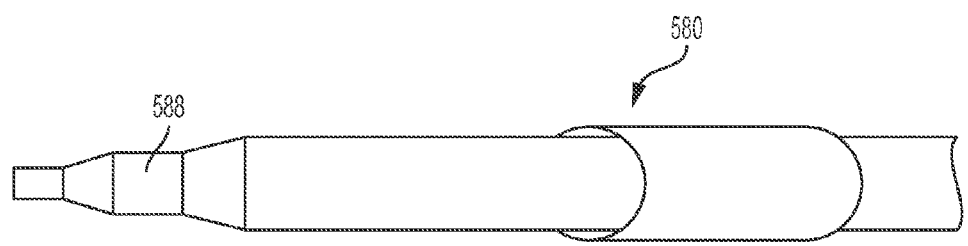
Figure 20M:
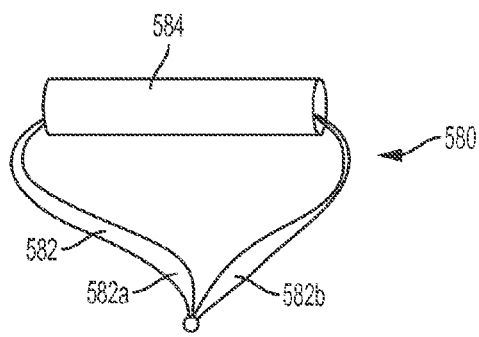

FIG. 20K illustrates another alternative tissue anchor (580) useful in the various systems and methods of the present teachings. This tissue anchor includes an elongate strip (582) that is similar to those described in FIGS. 20A-20D. Elements described in details in FIGS. 20A-20D can be incorporated in this alternative tissue anchor. For example, the tissue anchor (580) can include one or more holes (586) that are similar to holes (96) in FIGS. 20B and 20C, and configured to allow a tension member (590 in FIGS. 20N-20P) sliding through. Alternatively, a flexible tensioning member or suture (590 in FIGS. 20N-20P) can also be threaded with a needle through the elongated strip (582). In some embodiments, the tissue anchor (580) includes a band (584). In certain embodiments, the elongate strip (582) and the band (584) are arranged such that the band (584) slides relative to the elongate strip (582). This band can serve one or more of a plurality of purposes. For example, the band (584) can include one or more radiopaque markers. Accordingly, a tissue anchor (580) can be visualized in delivery and deployment under a radiographic imaging equipment such as X-ray, magnetic resonance, ultrasound, fluoroscope, or other imaging techniques. Alternative or in addition to the radiopaque markers, the band (584) can also assist to perforate the annulus. Or, alternatively or additionally, the band (584) can also assist to transition the tissue anchor from a delivery configuration as shown in FIGS. 20K and 20L to a deployed configuration as shown in FIG. 20M.

With respect to the components of the anchor, the band (584) has a number of cross-sections. In various embodiments, the cross-section of band (584) is cylindrical, rectangular, I-beam, annular, or any other practical shape. In addition, the band can be made of a material selected from a number of materials. In various embodiments, the band is made of a metal, including platinum, titanium, steel, or an alloy thereof. In various embodiment, the band is made of a polymer, including polyester, polypropylene, a co-polymer thereof, or a composite thereof.

The elongate strip (582 in FIGS. 20K-20P, as well as those in other embodiments) can be a sheet, cord, or another structure. In various embodiments, an elongate strip of the present teachings is made of a polymer, including polyester, polypropylene, a co-polymer thereof, or a composite thereof.

Similar to descriptions elsewhere in the present teachings, a tensioning member in relating to tissue anchors described herein can be a suture. In various embodiments, the tensioning member is a monofilament, a braided structure, a wire, or other structure that can be used to connect and tension multiple anchors. Typical tensioning materials include polyester, polypropylene, silk, and stainless steel.

Similar to the tissue anchors shown in FIGS. 20B-20D, in some embodiments, a tissue anchor also include a tip (588), as shown in FIG. 20L, which has one or more characteristics and/or functions discussed in relating to tip (76) in FIGS. 20B-20D.

FIG. 20M illustrates a tissue anchor of FIG. 20K or 20L in its deployed configuration. Specifically, after tissue anchor (580) is delivered to a location, tension is applied to the tensioning member and two terminal portions (582a and 582b) of the tissue anchor (580) fold into each other, as shown in FIG. 20M. In various embodiments, at least a part of band (584) is located in the right atrium or the right ventricle. In some embodiments, the entire band (584) is located in the right atrium. In some embodiments, the entire band (584) is located in the right ventricle. In various embodiments, at least a part of the elongate strip (582) is located in the right atrium or the right ventricle. In some embodiments, a least a part of the elongate strip (582) is located in the right atrium. In some embodiments, at least a part of the elongate strip (582) is located in the right ventricle. In various embodiments, at least a part of the elongate strip (582) is located through the tricuspid annulus. Without wishing to be bound by any particular theory, when a portion of the elongate strip (582), for example, the terminal portions (582a, or 582b, or 582a and 582b), is located through the tricuspid annulus, the possibility or the extent of tissue damage, for example, caused by a tissue anchor tearing through the annulus tissues, can be reduced or eliminated.

Figures 20N, 20O:
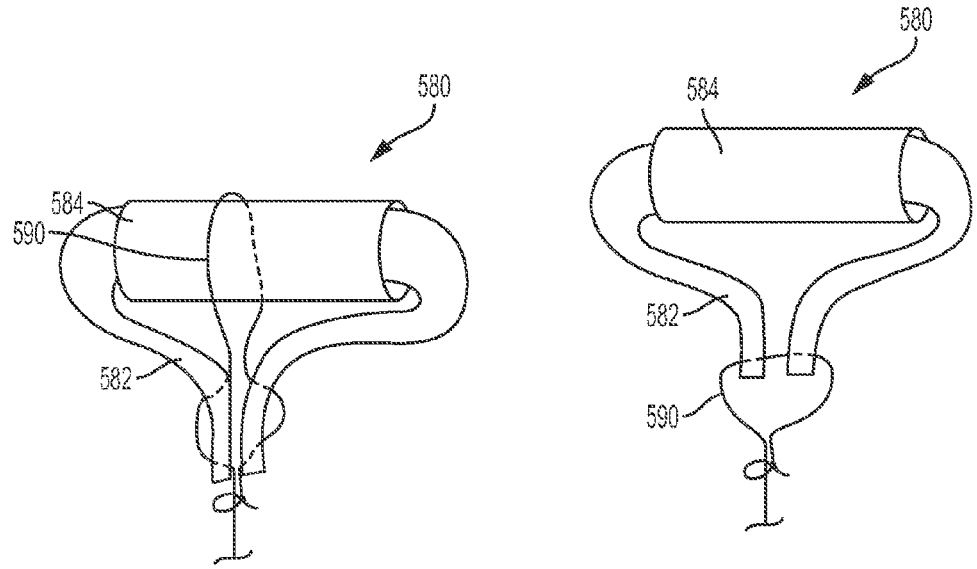

FIGS. 20N and 20O illustrate two alternative tissue anchors in their deployed configuration. In both the tissue anchors, each includes band (584), elongate strip (582), and tensioning member (590). In both the examples, the tensioning member travels through the strip. While the tissue anchor in its delivery profile, the tensioning member is relaxed to allow the string maintain its elongated profile. While the tissue anchor in its deployed profile, the tensioning member tightens to bring the ends of the strip together, transitioning into a deployed configuration. According to some embodiments, a knot or constraint is incorporate into the tensioning member near one end of the strip and the other end of the strip is allowed to slide freely along the tensioning member. When tension is applied, the knot or the constraint pushes the one end of the strip toward the other and transitions the tissue anchor into its deployed configuration. A person with ordinary skill in the art will appreciate that other arrangements of tensioning member are within the scope of the present teachings as long as they perform similar function in similar ways to yield similar results and are practical.

Referring back to FIGS. 20N and 20O, the difference between the two tissue anchors is the configuration of tensioning member (590) in relation to the band (584) and elongate strip (582): in FIG. 20N, tensioning member (590) extends through one end of elongate strip (582), over band (584), and through the other end of elongate strip (582); and in FIG. 20O, tensioning member (590) extends through one end of elongate strip (582) and through the other end of elongate strip (582). Thus, when tension is applied to the tissue anchor in FIG. 20N through the free end of tensioning member (590), it is also applied to the band (584); and when tension is applied to the tissue anchor in FIG. 20O, it pulls elongate strip (582), for example, such that one or both of the ends of elongate strip can be pulled through the annulus tissue.

Figure 20P:
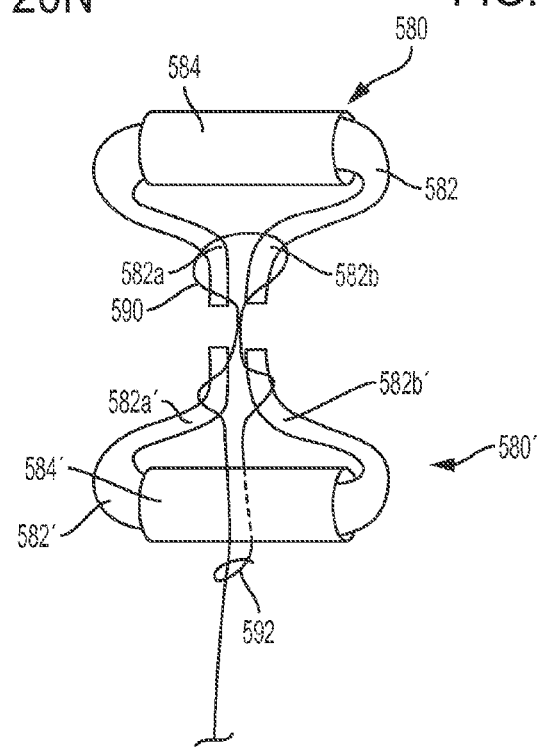

FIG. 20P illustrates another embodiment of tissue anchor according to the present teachings. This use includes a set of two tissue anchors (580 and 580') deployed at a first treatment location with a first end of tensioning member (590) extends through a first end (582a') of a first elongate strip (582'), a first end (582a) of a second elongate strip (582), a second end of the second elongate strip (582), and a second end of the first elongate strip (582'). In addition, the first end of tensioning member (590) extends from a side of band (584) that is different from where a second end of the tensioning member (590) extends and form a knot around the second end of tensioning member (590). Thus, when tension is applied to the second end (the free end) of tensioning member, tissue anchors (580 and 580') are pulled towards each other. In addition, the two ends of elongate strip (582) of tissue anchor (580) can be pulled through annulus tissues and the band (584') of tissue anchor (580') can be pressed against the tissues. A person with ordinary skill in the art will appreciate that other arrangements and/or uses of tensioning member are also within the scope of the present teachings.

Examples of a tissue anchor (580 and 580') described in conjunction with the above drawings of the present teachings have some similarities to those in U.S. patent application Ser. No. 12/557,655, filed on Sep. 11, 2009, entitled Tissue Plication Device and Method for Its Use, which is incorporated by reference herein in its entirety.

Tissue Plications

Another aspect of the present teachings relates to placating tissues by using two or more tissue anchors of the present teachings. FIGS. 21A-21C illustrate an embodiment of a plication procedure, for example, for reducing the circumference of a tricuspid valve annulus (40a). In this regard, a single tensioning member, such as a suture (103) or other member may be used to deploy, fasten, and draw together at least two separate tissue anchors (110). This sometimes is referred to a chain plication.

As shown in FIG. 21A, first and second tissue anchors (110) may be respectively deployed at spaced apart locations along the tricuspid valve annulus (40a). Each tissue anchor (110) includes an elongate strip (114) of flexible material, such as fabric or other material as described herein, as well as a single suture (103) or tensioning member extending through each of the elongate strips (114). Upon deployment of the two tissue anchors (110) through the tissue layer (40) at spaced apart locations, the free end of the suture (103) or tensioning member is pulled thereby securely fastening the first tissue anchor (110) as shown in FIGS. 21A and 21B and subsequently securely fastening the second tissue anchor (110) to the annulus tissue (40a). Upon further pulling or tensioning of the suture (103), the tissue anchors (110) will be drawn together to plicate the tissue (40) therebetween as shown in FIG. 21C. A crimp or other locker member (116) may then be used to lock in the desired amount of plication by crimping onto the free end of the suture (103). The excess suture (103) may then be cut to eliminate or reduce the length of the suture tail.

Figure 22A:
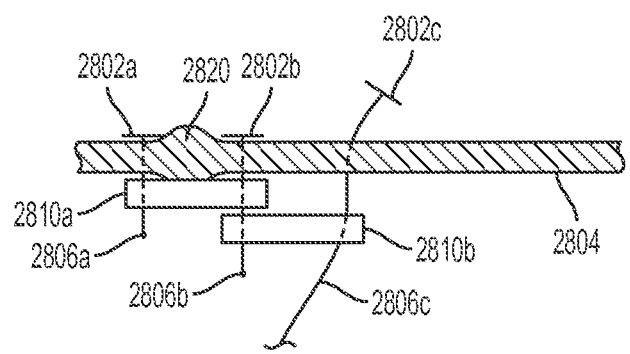
FIGS. 22A and 22B are representations of an alternative embodiment of tissue anchors and lockers which are used in an exemplary process of creating a chain of plications in accordance with the present teachings.
Figure 22B:
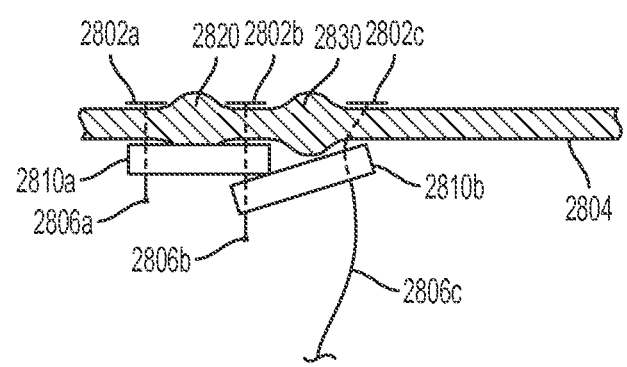

FIGS. 22A-22B illustrate another embodiment of a plication procedure of the present teachings, for example, for use during annuloplasty on a tricuspid valve annulus (40a). As shown in FIG. 22A, a first anchor (2802a), which may be a T-bar, has a tail (2806a), such as a suture, and is anchored to tissue (2804). Typically, tissue (2804) is tissue of a tricuspid valve annulus or tissue near a tricuspid valve. A second anchor (2802b), which has a tail (2806b) is also anchored into tissue (2804). Typically, the distance between second anchor (2802b) and first anchor (2802a) is a measured distance, i.e., the distance between second anchor (2802b) and first anchor (2802a) is predetermined. In one embodiment, the distance is substantially controlled using a catheter.

Once first anchor (2802a) and second anchor (2802b) are in place, a bar locker (2810a) is delivered over tails (2806a, 2806b), as shown in FIG. 22B. According to some embodiments, the length of the bar lock is smaller than the distance between the two implantation locations. Thus, once the bar locker (2810a) is delivered and secured to the tails of the first and second tissue anchors (2806a, 2806b), the distance between the two tissue anchors are reduced and a first plication (2820) is then effectively created. According to some embodiments, a third tissue anchor is implanted at a third treatment location, and a second bar lock is then delivered and secured to the tails of the second and third tissue anchors, a second plication is then created. One skilled in the art would understand, by repeating these steps, a chain of plications is then created.

It should be appreciated that if tail (2806) is also locked and trimmed, then a chain of two plications (2820, 2830) is completed. Alternatively, if more plications are to be added, then additional anchors and lockers may be positioned as appropriate such that tail (2806c) serves as a "starting point" for the additional plications.

Figure 23A:
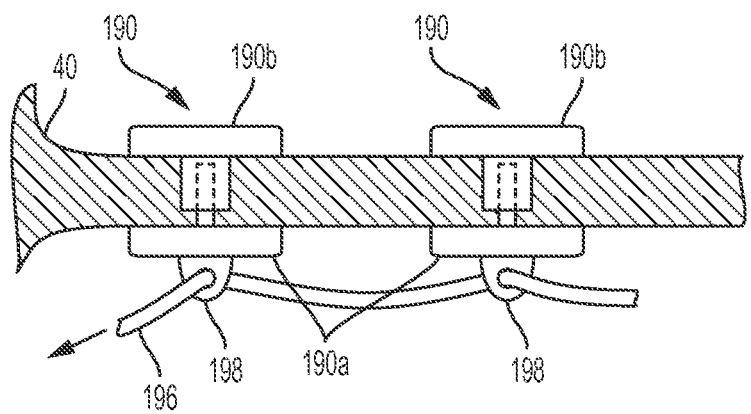
FIGS. 23A and 23B illustrate another alternative embodiment of tissue anchors chained together by a tensioning member to plicate the tissue between the tissue anchors according to the present teachings.
Figure 23B:
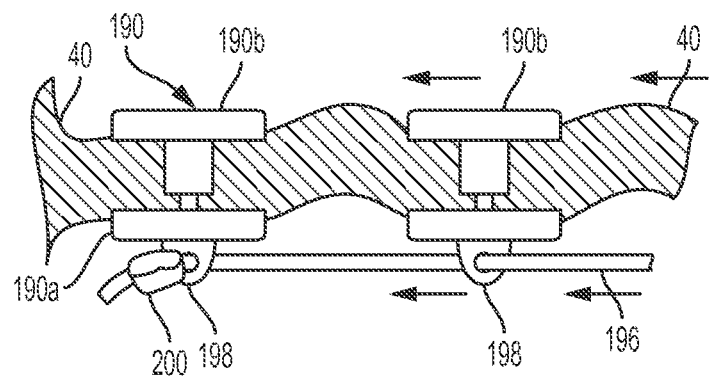

FIGS. 23A-23B illustrate another embodiment of a plication procedure according to the present teachings. In this embodiment, tissue anchors (190) in the form of anchor buttons (190a) are placed along the annulus (40). Although not shown, a catheter is used to deliver and implant a series of anchor buttons across the annulus. As described above, the anchor buttons could be implanted across the tricuspid annulus from ventricle to atrium, or alternatively, from atrium to ventricle. According to some embodiments, anchor buttons (190a) are further coupled to a flexible tensioning member (196). During delivery, the flexible tensioning member slidably is disposed within attachment means, for example, eyelets as illustrated in FIGS. 23A-23B. The distal end of the tensioning member incorporates a constraining mechanism, including a knot or a crimp, which can stop the first anchor button from sliding off. Upon deployment, the tensioning member is pulled from its proximal end. The constraining mechanism at the distal end of the tensioning member applies a force to the first anchor button and reduces the distance between the first and last anchor buttons. By further stopping the relative movement between the last anchor button and the tensioning member, e.g., by a crimp or a slip knot, the tricuspid annulus is plicated and its circumference is reduced. In some embodiments, the flexible tensioning member is located in the right atrium. In some embodiments, the flexible tensioning member is located in the right ventricle.

Figure 24A:
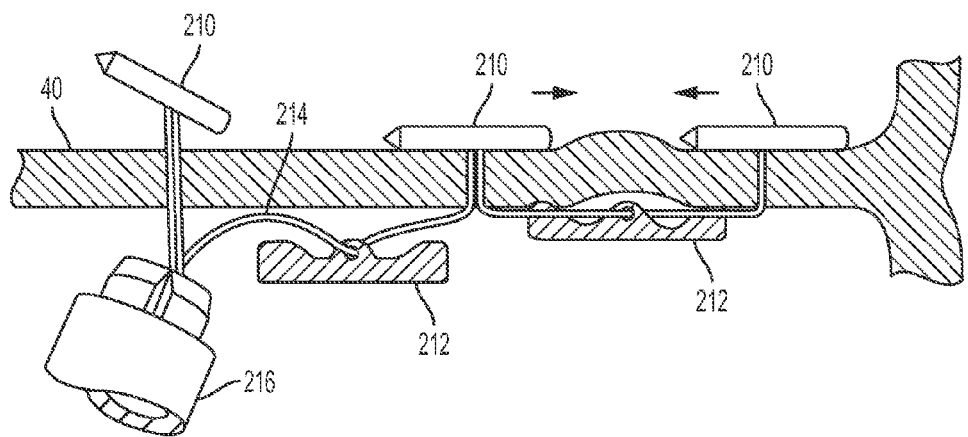
FIGS. 24A-24C illustrate yet another alternative embodiment of tissue anchors chained together by a tensioning member to plicate the tissue between the tissue anchors according to the present teachings.
Figure 24B:
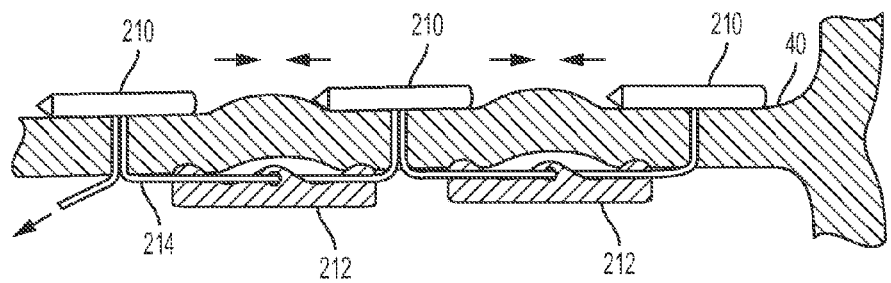
Figure 24C:
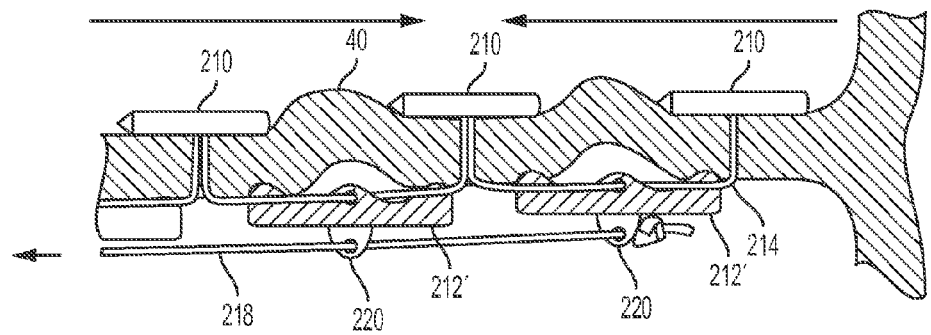

FIGS. 24A-24C illustrate another embodiment of a plication procedure according to the present teachings. Specifically, FIGS. 24A-24B illustrate the placement of tissue anchors (210) on the right atrial side of the tricuspid valve, chained to pledgets or fasteners (212) in the form of tissue trapping load spreading members underneath the annulus (40). These anchors and fasteners (210, 212) are coupled together by a flexible tensioning member (214) or drawstring, in this case. A catheter (216 in FIG. 24A) is used to deliver tissue anchors and fasteners (210, 212) in a serial fashion along flexible tensioning member (214) such that tissue anchors (210) are driven through the tissue and fasteners (212) are released between each tissue anchor (210). According to some embodiments, the tensioning member slidably is disposed through tissue anchors and fasteners. According to some embodiments, the tissue anchors and fasteners are deployed on the opposite sides of the annulus tissue. The catheter approaches the annulus from one side and deploys a tissue anchor across the annulus and on the other side of the tissue. The series of tissue anchors and fasteners (210, 212) is then drawn together using the drawstring or flexible tensioning member (214) as shown in FIG. 24B. This shortens the distance between each of the tissue anchors and fasteners (210, 212) and the entire structure with elements above and below the annulus (40). The tissue becomes trapped between the tissue anchors and fasteners (210, 212) spreading loads over larger areas and reducing tear out risks. Similarly to FIGS. 22A-22B, in some embodiments, the tissue anchors (210) are located in the right ventricle. In other embodiments, the tissue anchors (210) are located in the right atrium.

FIG. 24C illustrates a modified version of the system illustrated in FIGS. 24A-24B. The tissue anchors and fasteners are fixedly connected to each other. And the fasteners further contains an eyelet (220) for a tensioning member to thread through. According to some embodiments, the tensioning member (218) is coupled to eyelets (220) in each of the fasteners (212'). According to some embodiments, the tensioning member is configured to be tensioned to reduce the circumference of the tricuspid annulus (40). In this embodiment, after the tissue anchors and fasteners are delivered and deployed, the tensioning member (218) is pulled to tighten the various tissue anchors and fasteners (210, 212') and plicate the annulus (40). Similarly to FIGS. 22A-22B, in some embodiments, the tissue anchors are located in the right ventricle. In other embodiments, the tissue anchors are located in the right atrium.

Figure 25A:
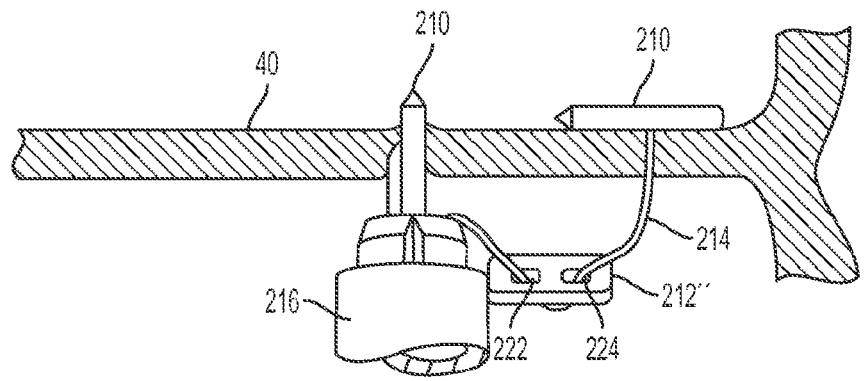
FIGS. 25A-25C illustrate yet another alternative embodiment of tissue anchors chained together by a tensioning member to plicate the tissue between the tissue anchors according to the present teachings.
Figure 25B:
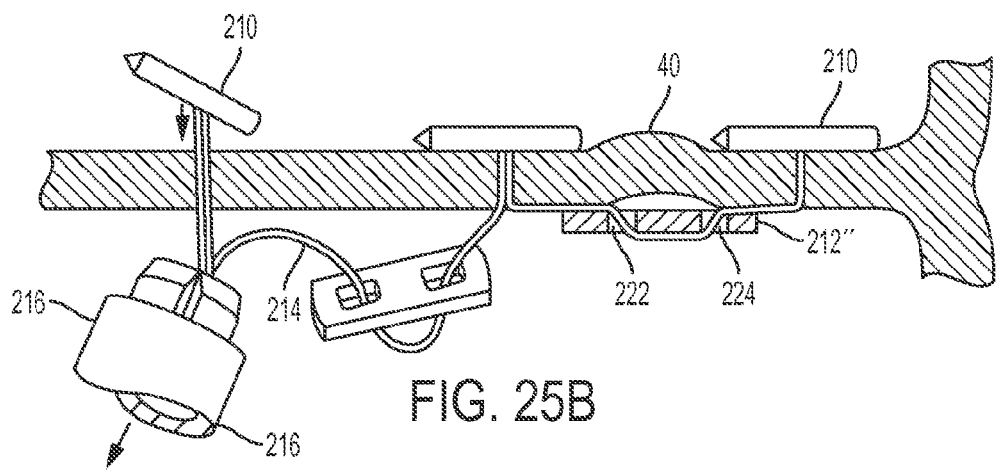
Figure 25C:
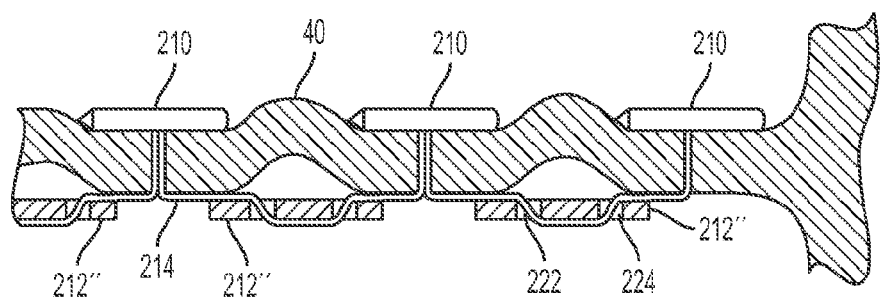

FIGS. 25A-25C illustrate an alternative embodiment a plication procedure according to the present teachings. This embodiment is somewhat similar to FIGS. 24A-24B, except that the fasteners (212") have a pair of holes (222, 224) through which the flexible tensioning member (214) or drawstring is threaded, as opposed to an eyelet structure.

Figure 26A:
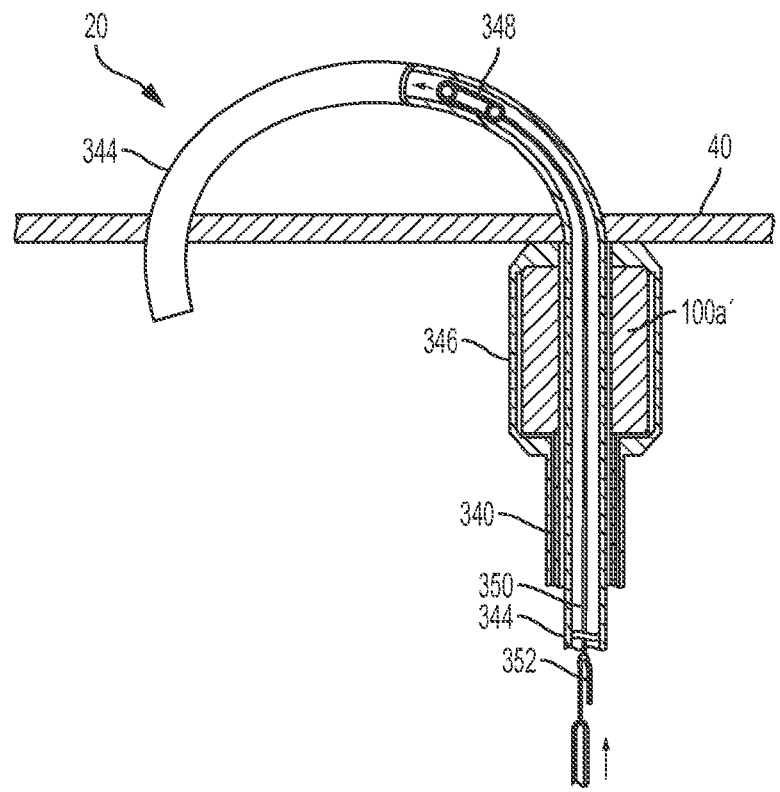
FIGS. 26A-26E illustrate yet another alternative embodiment of tissue anchors chained together to plicate the tissue between the tissue anchors according to the present teachings.
Figure 26B:
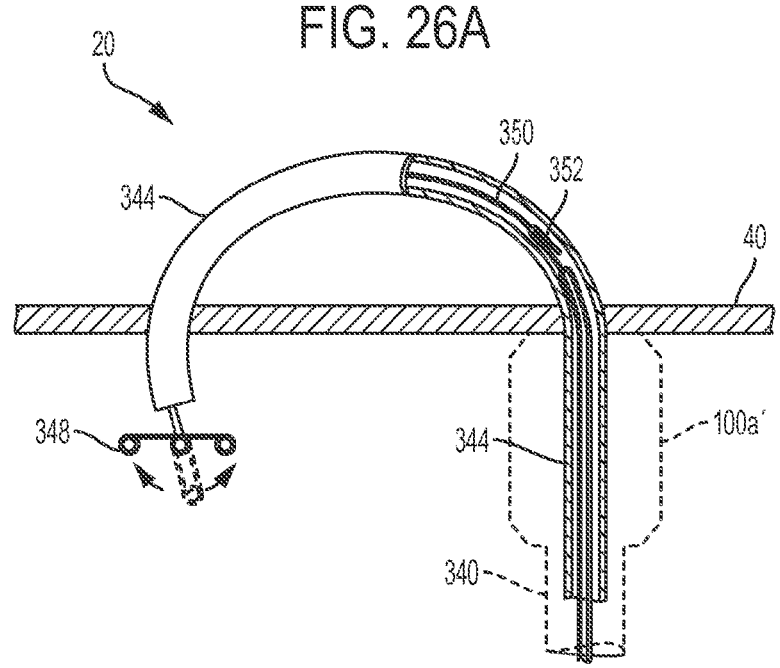
Figure 26C:
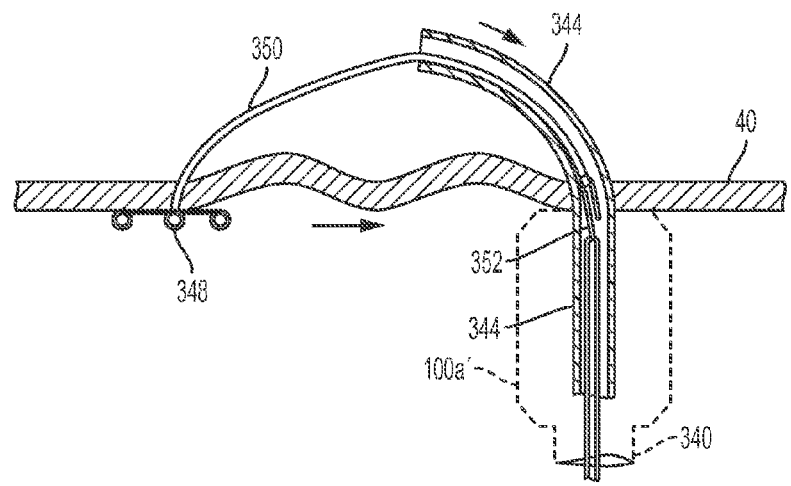
Figure 26D:
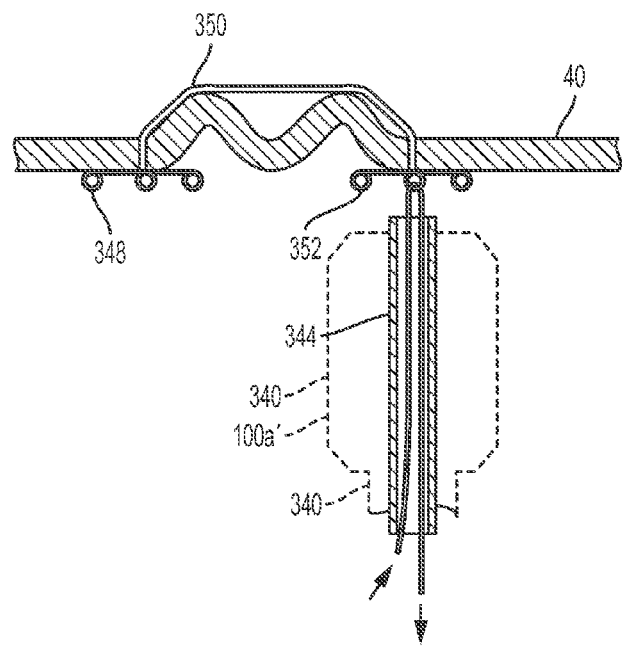
Figure 26E:
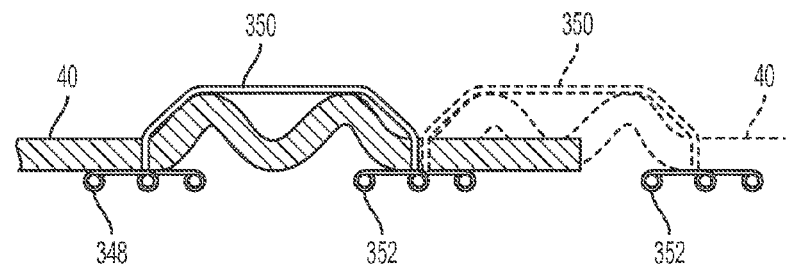

FIGS. 26A-26E illustrate an alternative embodiment of a plication procedure according to the present teachings. This embodiment includes a catheter based system for applying a series of tissue anchors through tissue generally at the tricuspid valve annulus. As shown in FIGS. 26A-26D, a tissue anchor (348) is delivered through the lumen of the steerable catheter portion (344) and is coupled with a flexible tensioning member (350) and another tissue anchor (352). The first and second fasteners (348, 352) are deployed on the same side of the tissue (40) at spaced apart locations with the flexible tensioning member (350) coupled therebetween. These tissue anchors (348, 352) may be formed essentially as torsion spring members which may have a portion which captures and locks against the flexible tensioning member (350) in the deployed position as shown in FIG. 26D. Once the first tissue anchor (348) is deployed as shown in FIGS. 26A-26C, the flexible tensioning member (350) may be pulled to plicate the tissue (40) between the first tissue anchor (348) and the steerable catheter portion (344). At this time, the second tissue anchor (352) is delivered and captures and locks with the flexible tensioning member (350) to lock the length of the flexible tensioning member (350) between the two tissue anchors (348, 350) with the tissue plicated as shown in FIG. 26D. This process may be repeated, as necessary, to plicate additional annulus tissue (40) for further annulus reduction, for example, as shown in FIG. 26E.

Figure 27A:
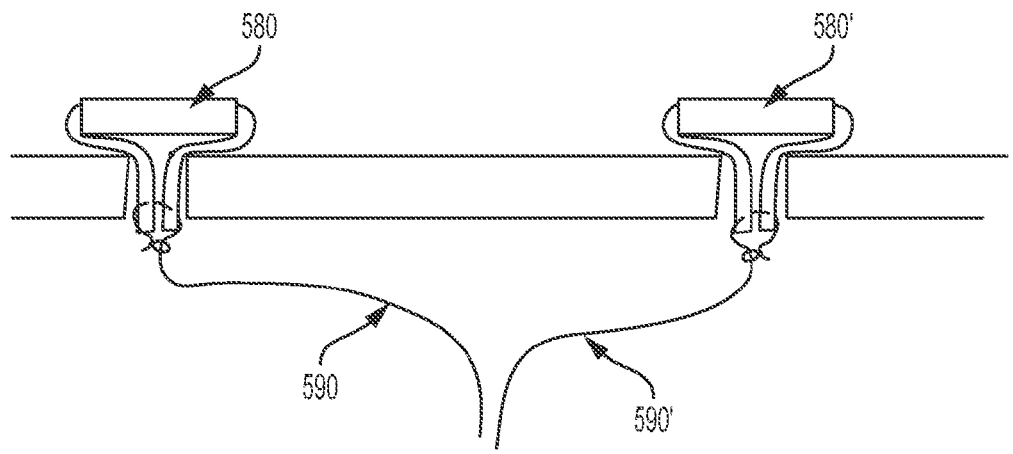
FIGS. 27A and 27B illustrate yet another alternative embodiment of tissue anchors chained together to plicate the tissue between the tissue anchors according to the present teachings.
Figure 27B:
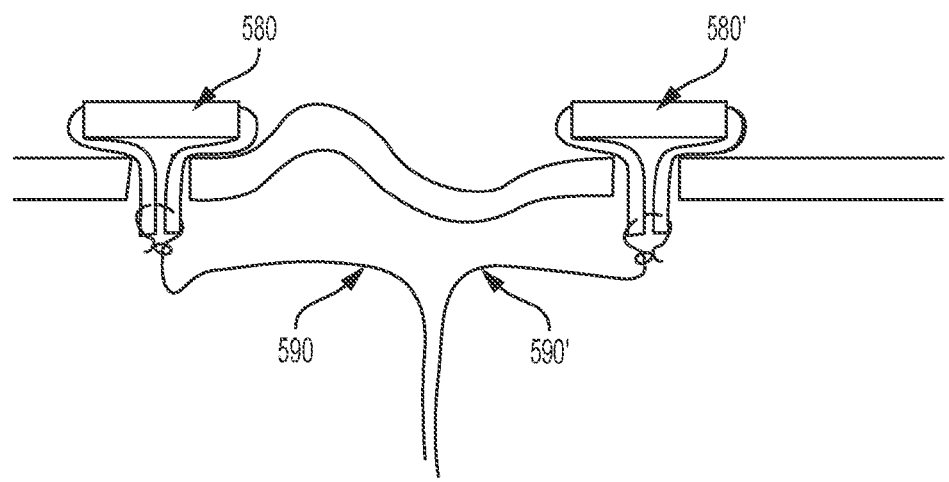

FIGS. 27A and 27B illustrate yet another embodiment of a plication procedure according to the present teachings. In this exemplary procedure, tissue anchors shown in FIGS. 20K-20P are used. Specifically, in some embodiments, after two tissue anchors (580 and 580') are deployed on the tricuspid valve along the tricuspid annulus, tension is applied to tensioning members (590 and 590') and, as a result, the distance between the two tissue anchors are reduced and the tissue between the two tissue anchors (580 and 580') are plicated, as shown in FIG. 27B. At this point, a locker or crimp can be applied to the free ends of flexible tensioning members to maintain the plication. Additional tissue anchors can be used for further annulus reduction. Alternatively, tissue anchors (580 and 580) can be connected to a single flexible tensioning member, similar to those in FIGS. 21A-21C. By applying tension to the tensioning member, the tissue anchors (580 and 580') are pulled together and the tissue between the tissue anchors (580 and 580') is plicated.

Although several exemplary chain plications are described herein, one with ordinary skill in the art would understand that other devices, for example, including tissue anchors, fasteners, tensioning members, and the like, can be used without departing from the letters and spirit of the present teachings. The chain plication described in conjunction with the drawings of the present teachings have some similarities to those in U.S. patent application Ser. No. 10/948,923, filed on Sep. 24, 2004, entitled Tissue Fastening Systems and Methods Utilizing Magnetic Guidance; U.S. patent application Ser. No. 10/689,872, filed on Jun. 11, 2013, entitled Method and Apparatus for Performing Catheter-based Annuloplasty Using Local Plications; and U.S. patent application Ser. No. 11/174,951, filed on Jun. 5, 2005, entitled Tissue Anchor, Anchoring System and Methods of Using the Same; each of which is incorporated in its entirety by reference herein.

Chain Tissue Anchor Delivery System

Another aspect of the present teachings relates to a chain tissue anchor delivery system that can be used in delivering and/or deploying a chain of tissue anchor and/or plicating tissues as discussed herein. In various embodiments, a delivery system delivers a series of connected tissue anchors to a series of treatment locations along a tricuspid annulus as discussed herein. An example of such delivery and deployment is illustrated in FIGS. 13A and 13B. In various embodiments, the chain tissue anchor delivery system delivers two or more tissue anchors to two or more different locations. In some embodiments, the chain tissue anchor delivery system delivers and deploys one, two, three, four, five, six, or more tissue anchors in a sequential manner. Thus, after such delivery, as the tensioning member is pulled or tightened, these two or more tissue anchors are pulled more closely and tissues between each pair of the tissue anchors are plicated.

Figure 28A:
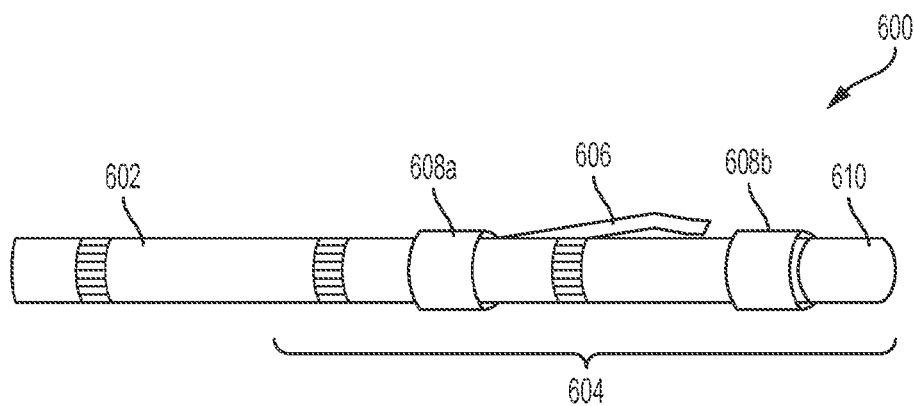
FIGS. 28A and 28B illustrate a distal portion of an exemplary push wire according to the present teachings.

In various embodiments, a chain tissue anchor delivery system, as shown in FIG. 28A, includes an elongate shaft (602) having a distal portion (604). As a person with ordinary skill in the art will understand, the elongate shaft (602) extends proximally (to the left in FIG. 28A) and, when in use, a proximal end of the elongate shaft (602) extends within a catheter lumen, in some cases, throughout the catheter and outside the body of a patient. In various embodiments, a clinician controls and manipulates the proximal end (not shown) so that the chain tissue anchor delivery system (600) can extend, withdraw, capture, release, and perform any other functions that it possesses. In some embodiments, the control and manipulation is through additional mechanisms that are generally known by the skilled artisan.

In various embodiments, the chain tissue anchor delivery system, as shown in FIG. 28A, includes a tissue anchor holder (606). According to some embodiments, the tissue anchor holder (606) has a fixed end attaching to the elongate shaft (602), and a free end. The tissue anchor holder (606) is configured to deflect at or near its fixed end. The free end of the tissue anchor holder is positioned distally to the fixed end. Thus, in some embodiments, the tissue anchor holder (606) has a first configuration where its free end stays close to the body of the elongate shaft (602). In some embodiments, the tissue anchor holder (606) has a second configuration where the holder deflects radially outwardly and its free end is radially away from the body of the elongate shaft (602).

Figure 28B:
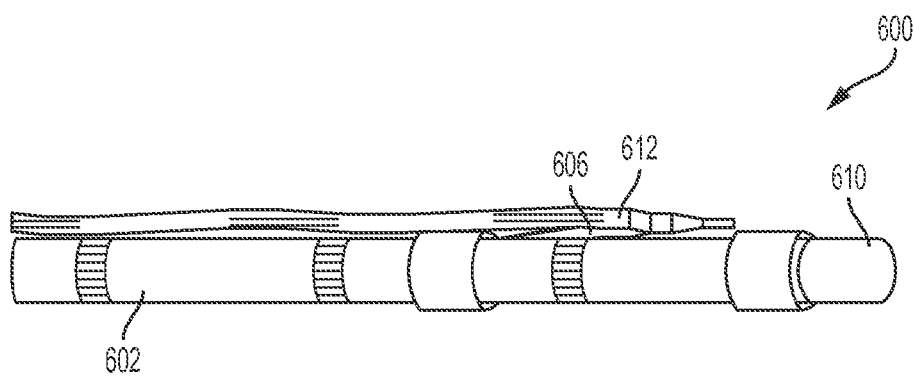

According to some embodiments, when the tissue anchor holder (606) captures a tissue anchor (612), as shown in FIG. 28B, it deflects radially away and its free ends is pushed radially outwardly by the anchor, and assumes its second configuration. Once the tissue anchor is removed, the tissue anchor holder (606) assumes its first configuration with its free end returning to its radially inward position, close to the elongate shaft (602). At the second configuration, for example, the tissue anchor holder (606) retains a tissue anchor (612) and can be used to deliver the retained tissue anchor to a location, as discussed in detail elsewhere in the present teachings.

According to some embodiments, during a chain tissue anchor delivery, the tissue anchor holder (606) is positioned alongside the elongated tissue anchor. To capture the tissue anchor for delivery, according to some embodiments, a clinician pulls the elongate shaft (602) proximally first so the free end of the tissue anchor holder (606) is somewhat proximal to the distal end of an elongated tissue anchor. As the clinician subsequently pushes the elongate shaft (602) distally, the free end of the tissue anchor holder (606) captures the tissue anchor, for example, by capturing the fabric of the tissue anchor. To deploy the tissue anchor, the clinician extends the elongate shaft (602) distally, for example, across the annulus. As the clinician pushes the elongate shaft (602) distally, the distal end of the tissue anchor is pulled outside of the delivery catheter. According to some embodiments, the clinician then retracts the elongate shaft (602) proximally, for example, into the delivery catheter, which releases the tissue anchor. The tissue anchor can then be deployed fully, similar to what has been described above.

According to other embodiments, the elongate shaft (602) is then repositioned so that the tissue anchor holder (606) is configured to capture another tissue anchor for deployment. One skilled in the art would understand that the above steps can be repeated as many times as necessary to deploy a plurality of anchors along the annulus. According to some embodiments, unlike embodiments described above where the tissue anchor is deployed by pushing out of the delivery catheter from its proximal end, the chain tissue anchor delivery system facilities the deployment of tissue anchors across the annulus by pulling the distal end of the tissue anchor in order for the tissue anchor to exit the delivery catheter.

According to some embodiments, the chain tissue anchor delivery system is configured to deliver tissue anchors at, on, or across a heart valve annulus as described herein. According to some embodiments, a tissue anchor is any one of those illustrated in FIGS. 20A through 25C. One skilled in the art would understand that the chain tissue anchor delivery system disclosed herein can be used with other tissue anchors that can be delivered by the chain tissue anchor delivery system pulling the distal ends of the tissue anchors. Thus, embodiments disclosed and described in the present teaching should not be viewed as limiting.

In various embodiments, the chain tissue anchor delivery system, again as shown in FIG. 28A, includes one, two, or more marker (608a and 608b) to aid visualization during a percutaneous procedure. In various embodiments, the chain tissue anchor delivery system, again as shown in FIG. 28A, includes a distal end (610). In some embodiments, the distal end (610) has a non-traumatic end, as shown in FIG. 28A. Thus, in some embodiments, the distal end (610) is configured to facilitate the chain tissue anchor delivery system to perforate tissues or expand an existing perforation in the tissues without damaging the tissues or surrounding tissues.

Figure 29A:
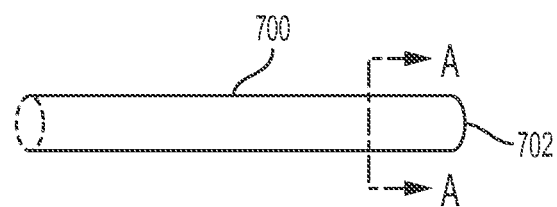
FIG. 29A illustrates a distal portion of an exemplary deliver catheter according to the present teachings.

FIG. 29A illustrates a distal portion of an exemplary catheter (700) according to the present teachings. The delivery catheter in FIG. 29A extends proximally (e.g., to the left according to this figure) and a proximal end can in many cases extend outside a patient's body. A delivery catheters can be used in delivering and deploying a tissue anchor of the present teachings, some of the examples shown in FIGS. 11-13. The distal portion of delivery catheter includes a distal end (702).

Figure 29B:
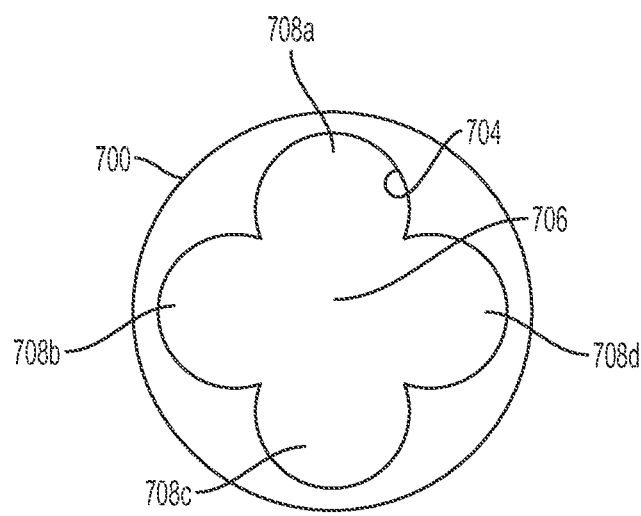
FIG. 29B illustrates a cross-sectional view of the distal portion of an exemplary deliver catheter in FIG. 29A according to the present teachings.

In various embodiments, a delivery catheter is used in combination with a chain tissue anchor delivery system of the present teachings. FIG. 29B shows a sectional view of such catheter taken along the A-A line in FIG. 29A. In these particular embodiments, the delivery catheter includes a lumen (704) having a central lumen (706) and four side lumens (708a, 708b, 708c, and 708d) and each of the four side lumens (708a, 708b, 708c, and 708d) is in fluid communication with the central lumen (704). Solely for ease of discussion, each of the central lumen and four side lumens has an imaginary center or origin. In various embodiments, the distances between each imaginary center of the four side lumens (708a, 708b, 708c, and 708d) and the imaginary center of the central lumen (706) are the same. In various embodiments, the distances between each imaginary center of the four side lumens (708a, 708b, 708c, and 708d) and the imaginary center of the central lumen (706) are different. In some embodiments, two of the four distances are the same. In some embodiments, three of the four distances are the same. In some embodiments, all of the four distances are different. In various embodiments, the distance between the imaginary centers of a side lumen and the central lumen is no greater than the sum of the radiuses of the two lumens. In some embodiments, the distance is no less than one of the radiuses.

In some embodiments, the delivery catheter includes additional lumens besides lumen (704). Accordingly, the central lumen (706), in some embodiments, is concentric with the delivery catheter (700). In other embodiments, the central lumen (706) is eccentric relative to the delivery catheter (700).

In some embodiments, lumen (704) extends throughout the delivery catheter. In other embodiments, lumen (702) extends from the distal end (702) of the delivery catheter proximally for a certain distance. In these other embodiments, a second lumen having a different shape, size, or a combination thereof connects with this lumen and continues extends proximally.

Figure 29C:
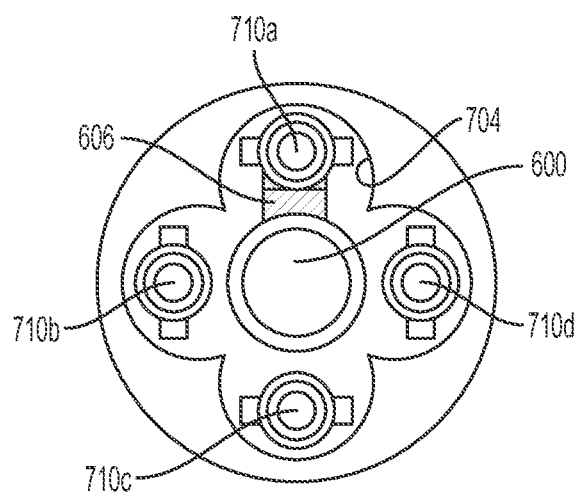
FIG. 29C illustrates a cross-sectional view of the distal portion of an exemplary delivery catheter in FIG. 29A with an exemplary push wire and exemplary tissue anchors slidably disposed in the exemplary delivery catheter according to the present teachings.

FIG. 29C is a sectional view of distal end of an exemplary delivery catheter, as shown in FIG. 29B, with tissue anchors (710a, 710b, 710c, and 710d) and chain tissue anchor delivery system (for example, 600 as shown in FIGS. 28A and 28B) disposed in lumen (704) of the catheter. Specifically, each of the tissue anchors (710a, 710b, 710c, and 710d) is disposed inside of one of the side lumens (708a, 708b, 708c, and 708d). In various embodiments, the tissue anchors (710a, 710b, 710c, and 710d) are in their elongated delivery configuration. In various embodiments, each of the four tissue anchors (710a, 710b, 710c, and 710d) is connected with a flexible tensioning member. In various embodiments, two of the four tissue anchors (710a, 710b, 710c, and 710d) are connected with a flexible tensioning member and these two tissue anchors are "chained." In various embodiments, three of the four tissue anchors (710a, 710b, 710c, and 710d) are connected with a flexible tensioning member and these three tissue anchors are "chained." In various embodiments, all of the four tissue anchors (710a, 710b, 710c, and 710d) are connected with a flexible tensioning member and these four tissue anchors are "chained."

Although FIGS. 29B and 29C show a lumen (704) having four side lumens (708a, 708b, 708c, and 708d), a person with ordinary skill in the art will appreciate that, as long as practical, tissue anchor delivery catheters each including lumen (704) with less than four (including 1, 2, or 3) or more than four (including 5, 6, 7, 8, 9, or 10) side lumens can be fabricated without undue experimentation and thus are also within the scope of the present teachings.

Thus, in various embodiments, in preparation, one, two, three, or four tissue anchors (710a, 710b, 710c, and 710d) in their delivery configuration are loaded into the corresponding side lumens (708a, 708b, 708c, and 708d). In some embodiments, a chain tissue anchor delivery system (600) is also loaded into the central lumen (706) in preparation. In other embodiments, a chain tissue anchor delivery system (600) is loaded after the delivery catheter is extended by a clinician to a location.

In various embodiments, after the delivery catheter is delivered to a first location according to FIG. 8B or 9B, a clinician opens the tissue anchor holder (606) in a chain tissue anchor delivery system (600) and extends the chain tissue anchor delivery system (600) to capture one of the plurality of tissue anchors (710a, solely for illustration purpose) as shown in FIG. 29C. In various embodiments, the clinician further extends the chain tissue anchor delivery system (600) so that its distal end (610) extends through an aperture on the annulus or perforates through tricuspid annulus, and deploys the tissue anchor, for example, by following the discussion relating to FIGS. 13A and 13B.

After the first tissue anchor is deployed, in various embodiments, the clinician retracts the chain tissue anchor delivery system (600) into the tissue anchor delivery catheter. In various embodiments, the clinician rotates the push wire (600) 90° or 180° either before or after the chain tissue anchor delivery system (600) is retracted into the catheter. In some embodiments, the rotation is achieved through additional mechanisms known to the skilled artisan. In other embodiments, the tissue anchor delivery catheter and the chain tissue anchor delivery system (600) are configured such that the chain tissue anchor delivery system (600) can be rotated by a clinician's rotation of a proximal end of the push wire outside the patient's body.

In various embodiments, the clinician retracts the chain tissue anchor delivery system (600) to a position approximately to one of the remaining tissue anchors (710*b*, solely for illustration purpose). In various embodiments, the clinician extends the chain tissue anchor delivery system (600) distally to capture one of the remaining tissue anchors (710*b*, solely for illustration purpose). In various embodiments, the clinician extends the chain tissue anchor delivery system (600) along with the tissue anchor (710*b*) captured by the holder (606) to a second location. In various embodiments, the clinician delivers the tissue anchor (710*b*) into the tricuspid annulus at the second location, as discussed in relation to FIGS. 12A and 12B.

The clinician can repeat the steps of retracting the elongate shaft, capturing a tissue anchors, and delivering and deploying the tissue anchor to secure additional tissue anchors (in this particular embodiment, the third and fourth tissue anchors (710*c* and 710*d*)) in the tricuspid annulus. In other embodiments where lumen (704) includes less than or more than four side lumens, a clinician delivers and deploys two, three, five, six, seven, eight, nine, or more tissue anchors by repeating the above steps. In various embodiments, each of the plurality of tissue anchors is connected with a tensioning member. In various embodiments, at least two of the plurality of tissue anchors are connected with a tensioning member. In some embodiments, all of the tissue anchors are connected with a tensioning member. Thus, a clinician can apply tension to the tensioning member to plicate tissues between each pair of the tissue anchors and reduce the circumference of the tricuspid valve.

According to various embodiments of the present teachings, a radiopaque marker or textured surface can be used to make the device visible by using a radiographic imaging equipment such as an X-ray, magnetic resonance, ultrasound or other imaging technique. A marker disclosed herein may be applied to any part of the guide, catheter, or devices disclosed in present teachings. A radiopaque marker can be sewed, adhered, swaged riveted, or otherwise placed and secured on the guide, catheter, and/or devices. The radiopaque marker may be made from a material selected from tantalum, tungsten, platinum, irridium, gold, an alloy thereof, or another material known to those with ordinary skill in the art. The radiopaque marker can also be made from cobalt, fluorione, or another paramagnetic material, or another MR visible material known to those with ordinary skill in the arts. Additionally, a contrast media injected into the atrium, ventricle, or artery may also be used to confirm the positioning under a fluoroscope.

Unless otherwise defined, all technical and scientific terms used herein have the same meaning as commonly understood by one of ordinary skill in the art to which this present teachings belong. Methods and materials similar or equivalent to those described herein can be used in the practice of the present teachings. In case of conflict, the specification, including definitions, controls. In addition, the materials, methods, and examples are illustrative only and not intended to be limiting.

We claim:

1. A method comprising:
    locating a first location near a heart valve annulus;
    advancing a tissue anchor delivery catheter to the first location, wherein the tissue anchor delivery catheter includes a deflectable tissue anchor holder that extends axially and longitudinally along an exterior of a shaft of the tissue anchor delivery catheter, the tissue anchor holder having a first end fixed to the shaft and an opposite free second end that is located distal to the first end, the second end of the tissue anchor holder configured to move radially outward from the shaft;
    capturing a first tissue anchor on the tissue anchor holder and deploying a distal portion of a first tissue anchor across the heart valve annulus at the first location;
    deploying a proximal portion of the first tissue anchor at the first location;
    locating a second location near the heart valve annulus;
    capturing a second tissue anchor on the tissue anchor holder and deploying a distal portion of a second tissue anchor across the heart valve annulus at the second location;
    deploying a proximal portion of the second tissue anchor at the second location;
        wherein the first tissue anchor and the second tissue anchor are connected with a continuous portion of a flexible tensioning member; and
    changing a distance between the first and second tissue anchors.

2. The method of claim 1, wherein at least one of the first and the second locations is on a tricuspid annulus.

3. The method of claim 2 comprising advancing a locating wire across the tricuspid annulus.

4. The method of claim 3 wherein the locating wire crosses the tricuspid annulus from right atrium to right ventricle.

5. The method of claim 3 wherein the locating wire crosses the tricuspid annulus from right ventricle to right atrium.

6. The method of claim 5 comprising capturing and pulling a distal end of the locating wire outside of the body.

7. The method of claim 3 comprising advancing a tissue anchor delivery catheter along the wire to the first location.

8. The method of claim 1, wherein the locating of the second location is after the deployment of the first tissue anchor.

9. The method of claim 1, wherein the locating of the second location is prior to the deployment of the first tissue anchor.

10. A method comprising:
    positioning a tissue anchor delivery catheter at a first location near a heart valve annulus, wherein the tissue anchor delivery catheter carries a plurality of tissue anchors;
    advancing a distal portion of a first tissue anchor outside of the tissue anchor delivery catheter across the annulus of the heart valve at the first location;
    deploying the distal portion of the first tissue anchor;
    advancing a proximal portion of the first tissue anchor outside of the tissue anchor delivery catheter at the first location;
    deploying the proximal portion of the first tissue anchor;
    positioning the tissue anchor delivery catheter at a second location near the heart valve annulus,
    advancing a distal portion of a second tissue anchor outside of the tissue anchor delivery catheter across the annulus of the heart valve at the second location;
    deploying the distal portion of the second tissue anchor;
    advancing a proximal portion of the second tissue anchor outside of the tissue anchor delivery catheter at the second location;
    deploying the proximal portion of the second tissue anchor;

wherein the first and second tissue anchors are connected with a continuous portion of a flexible tensioning member; and reducing a distance between the first and second tissue anchors;

wherein the distal portions of the first and second tissue anchors are advanced outside of the tissue anchor delivery catheter by a delivery system pulling on the distal portions of the first and second tissue anchors.

11. The method of claim 10, wherein the distal portion of the first and second tissue anchor is deployed inside the right atrium.

12. The method of claim 10, wherein the distal portion of the first and second tissue anchor is deployed inside the right ventricle.

13. The method of claim 10 further comprising locking the distance between the first and second tissue anchors.

14. A method comprising:
locating a first location near a heart valve annulus;
advancing a locating wire across a tricuspid annulus;
advancing a tissue anchor delivery catheter along the wire to the first location
deploying a distal portion of a first tissue anchor across the heart valve annulus at the first location;
deploying a proximal portion of the first tissue anchor at the first location;
locating a second location near the heart valve annulus;
deploying a distal portion of a second tissue anchor across the heart valve annulus at the second location;
deploying a proximal portion of the second tissue anchor at the second location;
wherein the first tissue anchor and the second tissue anchor are connected with a continuous portion of a flexible tensioning member; and
changing a distance between the first and second tissue anchors;
wherein at least one of the first and the second locations is on the tricuspid annulus;
wherein the tissue anchor delivery catheter comprises an elongated shaft with a tissue holder protruding outwardly and extending longitudinally along an outer surface of the elongated shaft, the tissue holder is a cantilevered structure with a free end that receives the first tissue anchor.

15. The method of claim 14, wherein a first portion of the first tissue anchor extends along the tissue holder and a second portion of the first tissue anchor extends along the outer surface of the elongated shaft proximal to an attachment point of the tissue holder to the elongated shaft.

16. The method of claim 14, wherein the elongated shaft includes a pair of spaced visualization markers, the tissue holder being disposed between the pair of spaced visualization markers.

17. The method of claim 14, wherein the free end of the tissue holder is located distal to an attachment point at which the tissue holder is attached to the elongated shaft.

18. The method of claim 14, wherein the tissue holder is configured to deflect radially outward from the elongated shaft.

19. The method of claim 14, wherein the tissue holder is configured to move between a first position and a second position, wherein in the first position, the tissue holder is free of the first tissue anchor and the free end assumes a radially inward position relative to the elongated shaft and wherein in the second position, the first tissue anchor is captured by the tissue holder which deflected radially outward and the free end is spaced radially from the elongated shaft.

* * * * *